United States Patent
Kolczewski et al.

(10) Patent No.: US 8,188,284 B2
(45) Date of Patent: *May 29, 2012

(54) 2-AMINOQUINOLINES

(75) Inventors: Sabine Kolczewski, Loerrach (DE); Claus Riemer, Freiburg (DE); Olivier Roche, Folgensbourg (FR); Lucinda Steward, Basel (CH); Juergen Wichmann, Steinen (DE); Thomas Woltering, Freiburg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 469 days.

This patent is subject to a terminal disclaimer.

(21) Appl. No.: 12/394,072

(22) Filed: Feb. 27, 2009

(65) Prior Publication Data

US 2009/0227583 A1    Sep. 10, 2009

(30) Foreign Application Priority Data

Mar. 7, 2008  (EP) .................................. 08152425

(51) Int. Cl.
*C07D 215/38* (2006.01)

(52) U.S. Cl. .... 546/159; 546/163; 514/313; 514/253.02

(58) Field of Classification Search .................. 546/159, 546/163; 514/313, 253.02
See application file for complete search history.

(56) References Cited

U.S. PATENT DOCUMENTS

| | | |
|---|---|---|
| 2007/0299074 A1 | 12/2007 | Netz et al. |
| 2009/0088451 A1* | 4/2009 | Kolczewski et al. .......... 514/313 |
| 2009/0227570 A1* | 9/2009 | Kolczewski et al. ....... 514/228.2 |
| 2009/0233927 A1* | 9/2009 | Kolczewski et al. ....... 514/235.2 |

FOREIGN PATENT DOCUMENTS

| | | |
|---|---|---|
| WO | WO 2003/045313 | 6/2003 |
| WO | WO 2004/080463 | 9/2004 |
| WO | WO 2004/096771 | 11/2004 |
| WO | WO 2005/082871 | 9/2005 |
| WO | WO 2007/022946 | 3/2007 |

OTHER PUBLICATIONS

Hoyer et al., Pharmacol. Rev. vol. 46, pp. 157-204 (1994).
Rees et al., FEBS Lett. vol. 355, pp. 242-246 (1994).
Francken et al., Eur. J. Pharmacol. vol. 361, pp. 299-309 (1998).
Noda et al., J. Neurochem. vol. 84, pp. 222-232 (2003).
Thomas, D. R., Pharmacol. Ther. vol. 111(3) pp. 707-714 (2006).
Doly et al., The Journal of Comparative Neurology vol. 476 pp. 316-329 (2004).
Dubertret et al., J. of Psychiatric Research vol. 35 pp. 371-376 (2004).
Garcia-Ladona et al., 36th Annual Meeting Soc. Neurosci. Oct. 14-18, Atlanta Abstract 33.1 (2006).
Drescher et al., 36th Annual Meeting Soc. Neurosci. Oct. 14-Oct. 18, Atlanta Abstract 33.2 (2006).
Thomas, Neuropharmacology vol. 51(3) pp. 566-577 (2006).
Barnes et al., Neuropharmacology vol. 38 pp. 1083-1152 (1999).
Pasqualetti et al., Mol. Brain Res. vol. 56 pp. 1-8 (1998).
Wang et al., Neurosci. Lett. vol. 278 pp. 9-12 (2000).
Birkett et al., Neuroreport vol. 11 pp. 2017-2020 (2000).
Iwata et al., Mol. Psychiatry vol. 6 pp. 217-219 (2001).
Duncan et al., Brain Research vol. 869, pp. 178-185 (2000).
Sprouse et al., Synapse, vol. 54(2) pp. 111-118 (2004).

* cited by examiner

*Primary Examiner* — D M Seaman
(74) *Attorney, Agent, or Firm* — George W. Johnston; Patricia S. Rocha-Tramaloni; Kimberly J. Prior

(57) ABSTRACT

The present invention relates to compounds of formula (I)

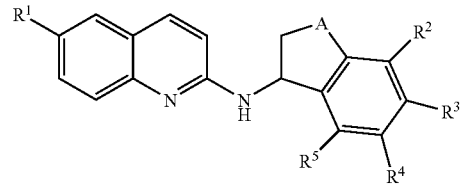

wherein A, $R^1$, $R^2$, $R^3$, $R^4$, and $R^5$ are as described herein, pharmaceutical compositions containing them, and methods for their manufacture. These compounds are $5\text{-HT}_{5A}$ receptor antagonists and are useful in the prevention and/or treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, abuse of drugs, motor disorders such as Parkinson's disease, psychiatric disorders or gastrointestinal disorders.

30 Claims, No Drawings

2-AMINOQUINOLINES

PRIORITY TO RELATED APPLICATION(S)

This application claims the benefit of European Patent Application No. 08152425.8, filed Mar. 7, 2008, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-HT$_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-HT$_{5A}$ serotonin receptor has been described in *FEBS Letters*, 355, 242-246 (1994). The sequence is not closely related to that of any previously known serotonin receptor, with the best homology being 35% to the human 5-HT$_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the 5-HT$_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The *Pharmacology & Therapeutics*, 111, 707-714 (2006) describes potential therapeutic utility of 5-HT$_{5A}$ receptor ligands for the treatment of circadian rhythm, sleep disturbances, mood disorders, schizophrenia, cognitive disorders and autism. The *Journal of Comparative Neurology*, 476, 316-329 (2004) suggests based on the localisation pattern of the 5-HT$_{5A}$ receptor in the rat spinal cord that 5-HT$_{5A}$ receptors may play a role in central motor control, nociception and autonomic function such as stress induced urinary incontinence and overactive bladder.

The *Journal of Psychiatric Research*, 38, 371-376 (2004) describes evidence for a potential significant role of the 5-HT$_{5A}$ gene in schizophrenia and more specifically in patients with later age at onset.

SUMMARY OF THE INVENTION

The present invention provides 2-aminoquinoline derivatives. In particular, the present invention provides compounds of formula (I)

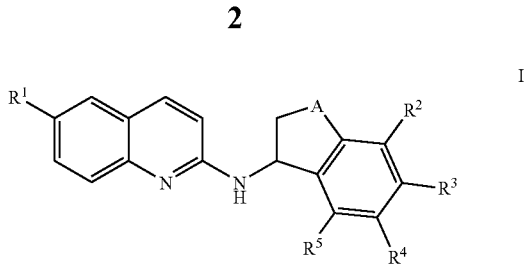

wherein
A is —CH$_2$— or —O—,
R$^1$ is 5-membered heteroaryl, —C(=NR$^a$)—Ar$^1$, —NR$^b$—Ar$^1$, —C(O)—NH—Ar$^1$, —NH—C(O)—Ar$^1$, —NH—S(O)$_2$—Ar$^1$, —NH—CH$_2$—Ar$^1$, —O—CH$_2$—Ar$^1$, —CH$_2$—NH—C(O)—Ar$^1$, —C(O)—NH—CH$_2$—Ar$^1$, —CH$_2$—NH—CH$_2$—Ar$^1$, —NH—S(O)$_2$—NR$^c$—Ar$^1$, —NR$^d$—C(O)—NR$^e$—Ar$^1$, —NH—C(O)—CH$_2$—Ar$^1$, —NH—C(O)—O—Ar$^1$, —NH—C(O)—NH—CHR$^f$—Ar$^1$, —NH—C(=NR$^a$)—NH—CH$_2$—Ar$^1$, —NH—(CH$_2$)$_3$—Ar$^1$, or —NH—C(S)—NH—C(O)—Ar$^1$,
R$^a$ is H, OH, or alkyl,
R$^b$, R$^c$, R$^d$, R$^e$, and R$^f$ are each independently H, alkyl, or allyl,
Ar$^1$ is phenyl or 5- to 10-membered monocyclic or bicyclic heteroaryl,
each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy,
R$^2$, R$^3$, R$^4$ and R$^5$ are each independently selected from H, halo, alkyl and alkoxy; or a pharmaceutically acceptable salt thereof.

The compounds of formula I can contain asymmetric carbon atoms. Accordingly, the present invention includes all stereoisomeric forms of the compounds of formula I, including each of the individual enantiomers and mixtures thereof, i.e. their individual optical isomers and mixtures thereof.

The present invention also provides pharmaceutical compositions containing a therapeutically effective amount of a compound of formula I or a pharmaceutically acceptable salt thereof and a pharmaceutically acceptable carrier. The invention further provides methods for the manufacture of the compounds and compositions of the invention.

Compounds of formula I have a good activity on the 5-HT$_{5A}$ receptor. Therefore, the invention provides compounds of formula I or pharmaceutically acceptable salts thereof as well as their use in the manufacture of medicaments for the treatment of depression (which term includes bipolar depression, unipolar depression, single or recurrent major depressive episodes with or without psychotic features, catatonic features, melancholic features, atypical features or post-partum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, panic disorders, agoraphobia, social phobia, obsessive compulsive disorders, post-traumatic stress disorders), psychotic disorders (which includes schizophrenia, schizoaffective disorders, bipolar disease, mania, psychotic depression, and other psychoses involving paranoia and delusions), pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, nicotine, benzodiazepines, alcohol (ethanol), caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "allyl" denotes a group —$CH_2CH=CH_2$.

As used herein, the term "alkyl" denotes monovalent linear or branched saturated hydrocarbon moiety, consisting solely of carbon and hydrogen atoms, having from 1 to 7 carbon atoms, for example, methyl, ethyl, propyl, isopropyl, n-butyl, iso-butyl, sec-butyl, tert-butyl and the like. Preferred alkyl groups are groups with 1, 2, 3 or 4 carbon atoms.

As used herein, the term "alkylene" means a linear saturated divalent hydrocarbon radical of one to seven carbon atoms or a branched saturated divalent hydrocarbon radical of three to seven carbon atoms. Preferred are divalent hydrocarbon radicals of one to four carbon atoms.

The term "halo" denotes chloro, iodo, fluoro and bromo. Preferred halo are fluoro, chloro and bromo.

The term "haloalkyl" denotes an alkyl group as defined above wherein at least one of the hydrogen atoms of the alkyl group is replaced by a halogen atom, preferably fluoro or chloro, most preferably fluoro. Examples of haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred haloalkyl groups are monofluoro-, difluoro- or trifluoro-methyl, -ethyl or -propyl, for example 3,3,3-trifluoropropyl, 2-fluoroethyl, 2,2,2-trifluoroethyl, fluoromethyl, trifluoromethyl. Particularly preferred is trifluoromethyl.

The term "hydroxyalkyl" denotes an alkyl group as defined above wherein at least one of the hydrogen atoms of the alkyl group is replaced by a hydroxy group. Examples of hydroxyalkyl include but are not limited to methyl, ethyl, propyl, isopropyl, isobutyl, sec-butyl, tert-butyl, pentyl or n-hexyl substituted by one or more OH, as well as those groups specifically illustrated by the examples herein below. Preferred is hydroxyethyl.

The term "cyanoyalkyl" denotes an alkyl group as defined above wherein at least one of the hydrogen atoms of the alkyl group is replaced by a cyano group. Examples of cyanoalkyl include but are not limited to methyl, ethyl, propyl, isopropyl, isobutyl, sec-butyl, tert-butyl, pentyl or n-hexyl substituted by one or more CN, as well as those groups specifically illustrated by the examples herein below.

The term "alkoxy" denotes a group —O—R' wherein R' is alkyl as defined above.

The term "aromatic" means the presence of an electron sextet in a ring, according to Hückel's rule.

The term "cycloalkyl" refers to a monovalent saturated monocyclic hydrocarbon radical of 3 to 7 ring carbon atoms, such as cyclopropyl, cyclobutanyl, cyclopentyl, cyclohexyl or cycloheptyl. Preferred are cyclopropyl, cyclopentyl and cyclohexyl. Cycloalkyl is optionally substituted as described herein.

The term "heterocycloalkyl" refers to a monovalent saturated 5- to 6-membered monocyclic ring system containing one, two or three ring heteroatoms selected from N, O and S, the remaining ring atoms being carbon atoms. "Heterocycloalkyl" can be unsubstituted or substituted as described herein. Examples of heterocycloalkyl moieties include, but are not limited to pyrrolidinyl, piperidinyl, piperazinyl, morpholinyl, or thiomorpholinyl. Preferred examples are piperidinyl and morpholinyl. Examples for substituents on heterocycloalkyl include, but are not limited to oxo, halo, alkyl, hydroxy, hydroxyalkyl, haloalkyl or alkyoxy.

"Heteroaryl" means a monocyclic or bicyclic monovalent aromatic ring system of 5 to 10 ring atoms containing one, two, or three ring heteroatoms selected from N, O, and S, the remaining ring atoms being C. Examples of heteroaryl moieties include, but are not limited to thiophenyl, furanyl, pyrrolyl, imidazolyl, pyrazolyl, oxazolyl, isoxazolyl, thiazolyl, isothiazolyl, [1,2,4]oxadiazolyl, [1,3,4]oxadiazolyl, [1,2,4]triazolyl, [1,2,3]triazolyl, tetrazolyl, pyridinyl, pyrimidinyl, pyrazinyl, pyridazinyl, indolyl, or benzoxazolyl. Preferred examples for heteroaryl are thiophenyl, imidazolyl, pyrazolyl, oxazolyl, isoxazolyl, thiazolyl, [1,2,4]oxadiazolyl, [1,3,4]oxadiazolyl, [1,2,4]triazolyl, tetrazolyl, pyridinyl, pyrimidinyl, indolyl, or benzoxazolyl. The heteroaryl ring can be optionally substituted as defined herein. Examples for substituents on heteroaryl include, but are not limited to halo, CN, $NO_2$, $NH_2$, OH, alkyl, haloalkyl, hydroxyalkyl, cyanoalkyl, cycloalkyl, -alkylene-cycloalkyl, -alkylene-O-alkyl, alkoxy, haloalkoxy, —$S(O)_2$-alkyl, —$S(O)_2$-cycloalkyl, —$SF_5$, or 5- to 6-membered heterocycloalkyl wherein heterocycloalkyl is optionally substituted as defined herein. Preferred substituents are halo, alkyl, haloalkyl, hydroxyalkyl, cycloalkyl, -alkylene-O-alkyl, alkoxy, —$S(O)_2$-alkyl, —$SF_5$, or 5- to 6-membered heterocycloalkyl wherein heterocycloalkyl is optionally substituted as defined herein.

Phenyl is unsubstituted or substituted with the same substituents as heteroaryl, or as further defined herein.

As used herein, the term "thiophenyl" is synonymous with "thienyl" and each represents a thiophene substituent, i.e., $C_4H_4S$.

When indicating the number of substituents, the term "one or more" means from one substituent to the highest possible number of substitution, i.e. replacement of one hydrogen up to replacement of all hydrogens by substituents. Thereby, one, two or three substituents are preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In detail, the present invention provides compounds of formula (I)

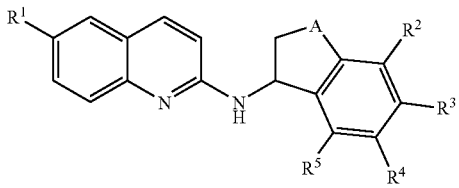

wherein

A is —CH$_2$— or —O—,

R$^1$ is 5-membered heteroaryl, —C(=NR$^a$)—Ar$^1$, —NR$^b$—Ar$^1$, —C(O)—NH—Ar$^1$, —NH—C(O)—Ar$^1$, —NH—S(O)$_2$—Ar$^1$, —NH—CH$_2$—Ar$^1$, —O—CH$_2$—Ar$^1$, —CH$_2$—NH—C(O)—Ar$^1$, —C(O)—NH—CH$_2$—Ar$^1$, —CH$_2$—NH—CH$_2$—Ar$^1$, —NH—S(O)$_2$—NR$^c$—Ar$^1$, —NR$^d$—C(O)—NR$^e$—Ar$^1$, —NH—C(O)—CH$_2$—Ar$^1$, —NH—C(O)—O—Ar$^1$, —NH—C(O)—NH—CHR$^f$—Ar$^1$, —NH—C(=NR$^a$)—NH—CH$_2$—Ar$^1$, —NH—(CH$_2$)$_3$—Ar$^1$, or —NH—C(S)—NH—C(O)—Ar$^1$, R$^a$ is H, OH, or alkyl, R$^b$, R$^c$, R$^d$, R$^e$, and R$^f$ are each independently H, alkyl, or allyl, Ar$^1$ is phenyl or 5- to 10-membered monocyclic or bicyclic heteroaryl,
  each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy, R$^2$, R$^3$, R$^4$ and R$^5$ are each independently selected from H, halo, alkyl and alkoxy;

or a pharmaceutically acceptable salt thereof.

In certain embodiments, A is —CH$_2$—.
In certain embodiments, A is —O—.
In certain embodiments, R$^1$ is as defined above.
In certain embodiments,
R$^1$ is imidazolyl,
  [1,2,4]-oxadiazolyl,
  [1,2,4]-triazolyl,
  —C(=NR$^a$)—Ar$^1$, wherein R$^a$ is OH, H or alkyl; preferably H or OH; more preferably OH,
  —NR$^b$—Ar$^1$, wherein R$^b$ is H or alkyl, preferably H,
  —C(O)—NH—Ar$^1$,
  —NH—C(O)—Ar$^1$,
  —NH—S(O)$_2$—Ar$^1$,
  —NH—CH$_2$—Ar$^1$,
  —O—CH$_2$—Ar$^1$,
  —CH$_2$—NH—C(O)—Ar$^1$,
  —C(O)—NH—CH$_2$—Ar$^1$,
  —CH$_2$—NH—CH$_2$—Ar$^1$,
  —NH—S(O)$_2$—NR$^c$—Ar$^1$, wherein R$^c$ is H or alkyl, preferably alkyl,
  —NR$^d$—C(O)—NR$^e$—Ar$^1$, wherein R$^d$ and R$^f$ are each independently H, alkyl, or allyl; preferably H,
  —NH—C(O)—CH$_2$—Ar$^1$,
  —NH—C(O)—O—Ar$^1$,
  —NH—C(O)—NH—CHR$^f$—Ar$^1$, wherein R$^f$ is independently H or alkyl,
  —NH—C(=NR$^a$)—NH—CH$_2$—Ar$^1$, wherein R$^a$ is OH, H or alkyl; preferably H or OH; more preferably H,
  —NH—(CH$_2$)$_3$—Ar$^1$, or
  —NH—C(S)—NH—C(O)—Ar$^1$,
and Ar$^1$ is as defined herein.

In certain embodiments,
R$^1$ is —NR$^b$—Ar$^1$, wherein R$^b$ is H or alkyl, preferably H,
  —NH—C(O)—Ar$^1$,
  —NH—S(O)$_2$—Ar$^1$,
  —NH—CH$_2$—Ar$^1$,
  —O—CH$_2$—Ar$^1$,
  —NH—S(O)$_2$—NR$^c$—Ar$^1$, wherein R$^c$ is H or alkyl, preferably alkyl,
  —NR$^d$—C(O)—NR$^e$—Ar$^1$, wherein R$^d$ and R$^f$ are each independently H, alkyl, or allyl; preferably H,
  —NH—C(O)—CH$_2$—Ar$^1$,
  —NH—C(O)—O—Ar$^1$, or
  —NH—C(O)—NH—CHR$^f$—Ar$^1$, wherein R$^f$ is independently H or alkyl,
and Ar$^1$ is as defined herein.

In certain embodiments, Ar$^1$ is phenyl or 5- to 10-membered monocyclic or bicyclic heteroaryl, each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

In certain embodiments, Ar$^1$ is phenyl or 5- to 10-membered monocyclic or bicyclic heteroaryl, each of which is unsubstituted or substituted by one or more halo, alkyl, haloalkyl, hydroxyalkyl, cycloalkyl, -alkylene-O-alkyl, alkoxy, —S(O)$_2$-alkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

In certain embodiments, Ar$^1$ is phenyl, thiophenyl, furanyl, pyrrolyl, imidazolyl, pyrazolyl, oxazolyl, isoxazolyl, thiazolyl, isothiazolyl, [1,2,4]oxadiazolyl, [1,3,4]oxadiazolyl, [1,2,4]triazolyl, [1,2,3]triazolyl, tetrazolyl, pyridinyl, pyrimidinyl, pyrazinyl, pyridazinyl, indolyl, or benzoxazolyl, each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

In certain embodiments, Ar$^1$ is phenyl, thiophenyl, imidazolyl, pyrazolyl, oxazolyl, isoxazolyl, thiazolyl, [1,2,4]oxadiazolyl, [1,3,4]oxadiazolyl, [1,2,4]triazolyl, tetrazolyl, pyridinyl, pyrimidinyl, indolyl, or benzoxazolyl, each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

In certain embodiments, $Ar^1$ is phenyl, thiophenyl, imidazolyl, pyrazolyl, oxazolyl, isoxazolyl, thiazolyl, [1,2,4]oxadiazolyl, [1,3,4]oxadiazolyl, [1,2,4]triazolyl, tetrazolyl, pyridinyl, pyrimidinyl, indolyl, or benzoxazolyl, each of which is unsubstituted or substituted by one or more halo, alkyl, haloalkyl, hydroxyalkyl, cycloalkyl, -alkylene-O-alkyl, alkoxy, —$S(O)_2$-alkyl, —$SF_5$, or 5- to 6-membered heterocycloalkyl.

In certain embodiments, $Ar^1$ is phenyl, [1,2,4]oxadiazol-3-yl, [1,2,4]oxadiazol-5-yl, [1,2,4]triazol-1-yl, [1,2,4]triazol-3-yl, [1,2,4]triazol-4-yl, [1,3,4]oxadiazol-2-yl, 1H-indol-4-yl, benzoxazol-2-yl, imidazol-1-yl, imidazol-2-yl, imidazol-4-yl, isoxazol-3-yl, oxazol-2-yl, pyrazol-3-yl, pyridin-2-yl, pyridin-3-yl, pyridin-4-yl, pyrimidin-2-yl, tetrazol-5-yl, thiazol-2-yl, thiazol-2-yl, thiazol-4-yl, or thiophen-2-yl, each of which is unsubstituted or substituted by one or more halo, CN, $NO_2$, $NH_2$, OH, alkyl, haloalkyl, hydroxyalkyl, cyanoalkyl, cycloalkyl, -alkylene-cycloalkyl, -alkylene-O-alkyl, alkoxy, haloalkoxy, —$S(O)_2$-alkyl, —$S(O)_2$-cycloalkyl, —$SF_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

In certain embodiments, $Ar^1$ is phenyl, [1,2,4]oxadiazol-3-yl, [1,2,4]oxadiazol-5-yl, [1,2,4]triazol-1-yl, [1,2,4]triazol-3-yl, [1,2,4]triazol-4-yl, [1,3,4]oxadiazol-2-yl, 1H-indol-4-yl, benzoxazol-2-yl, imidazol-1-yl, imidazol-2-yl, imidazol-4-yl, isoxazol-3-yl, oxazol-2-yl, pyrazol-3-yl, pyridin-2-yl, pyridin-3-yl, pyridin-4-yl, pyrimidin-2-yl, tetrazol-5-yl, thiazol-2-yl, thiazol-2-yl, thiazol-4-yl, or thiophen-2-yl, each of which is unsubstituted or substituted by one or more halo, alkyl, haloalkyl, hydroxyalkyl, cycloalkyl, -alkylene-O-alkyl, alkoxy, —$S(O)_2$-alkyl, —$SF_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

In certain embodiments, $R^2$, $R^3$, $R^4$ and $R^5$ are each independently selected from H, halo, alkyl and alkoxy.

In certain embodiments, $R^2$ is H and $R^4$ is H.

In certain embodiments, $R^3$ is H, halo; preferably H or fluoro.

In certain embodiments, $R^5$ is H, halo or alkoxy; preferably H, fluoro or methoxy.

In certain embodiments, $R^2$ is H, $R^3$ is H or halo, $R^4$ is H and $R^5$ is H, halo, or alkoxy.

It is to be understood that all embodiments as described above may be combined with each other.

Preferred compounds of present invention are those as exemplified below. Even more preferred are the following compounds:

(R)-Indan-1-yl-[6-(3-methoxy-benzyloxy)-quinolin-2-yl]-amine,
$N^2$—(R)-Indan-1-yl-$N^6$-pyridin-3-ylmethyl-quinoline-2,6-diamine,
$N^6$-(3-Imidazol-1-yl-propyl)-$N^2$—(R)-indan-1-yl-quinoline-2,6-diamine,
$N^2$—(R)-Indan-1-yl-$N^6$-(1H-indol-4-ylmethyl)-quinoline-2,6-diamine,
$N^6$-(1H-Imidazol-2-ylmethyl)-$N^2$—(R)-indan-1-yl-quinoline-2,6-diamine,
$N^2$—(R)-Indan-1-yl-$N^6$-thiazol-2-ylmethyl-quinoline-2,6-diamine,
4-Fluoro-N-[2-((R)-indan-1-ylamino)-quinolin-6-yl]-benzenesulfonamide,
$N^2$—(R)-Indan-1-yl-$N^6$-pyridin-4-ylmethyl-quinoline-2,6-diamine,
1-[2-((R)-Indan-1-ylamino)-quinolin-6-yl]-3-phenyl-urea,
$N^2$—(R)-Indan-1-yl-$N^6$-(5-methyl-3H-imidazol-4-ylmethyl)-quinoline-2,6-diamine,
$N^2$—(R)-Indan-1-yl-$N^6$-(1H-pyrazol-3-ylmethyl)-quinoline-2,6-diamine,
1-(4-Fluoro-phenyl)-3-[2-((R)-indan-1-ylamino)-quinolin-6-yl]-urea,
1-(3-Fluoro-phenyl)-3-[2-((R)-indan-1-ylamino)-quinolin-6-yl]-urea,
1-[2-((R)-Indan-1-ylamino)-quinolin-6-yl]-3-(4-methoxy-phenyl)-urea,
1-[2-((R)-Indan-1-ylamino)-quinolin-6-yl]-3-(3-methoxy-phenyl)-urea,
1-[2-((R)-Indan-1-ylamino)-quinolin-6-yl]-3-(2-methoxy-phenyl)-urea,
1-(2-Fluoro-phenyl)-3-[2-((R)-indan-1-ylamino)-quinolin-6-yl]-urea,
1-[2-((R)-Indan-1-ylamino)-quinolin-6-yl]-3-((R)-1-phenyl-ethyl)-urea,
1-[2-((R)-Indan-1-ylamino)-quinolin-6-yl]-3-((S)-1-phenyl-ethyl)-urea,
1-[2-((R)-Indan-1-ylamino)-quinolin-6-yl]-3-(4-methoxy-benzyl)-urea,
1-(6-Chloro-pyridin-3-yl)-3-[2-((R)-indan-1-ylamino)-quinolin-6-yl]-urea,
1-(2-Chloro-pyridin-4-yl)-3-[2-((R)-indan-1-ylamino)-quinolin-6-yl]-urea,
N-(4-chlorophenyl)-N'-{2-[(1R)-2,3-dihydro-1H-inden-1-ylamino]quinolin-6-yl}-N-methylsulfamide,
N'-{2-[(1R)-2,3-dihydro-1H-inden-1-ylamino]quinolin-6-yl}-N-(4-fluorophenyl)-N-methylsulfamide,
1-(3,5-Dimethyl-isoxazol-4-yl)-3-[2-((R)-indan-1-ylamino)-quinolin-6-yl]-urea,
1-[2-((R)-Indan-1-ylamino)-quinolin-6-yl]-3-(3-methyl-3H-imidazol-4-ylmethyl)-urea,
[2-((R)-Indan-1-ylamino)-quinolin-6-yl]-carbamic acid 4-methoxy-phenyl ester,
4-Fluoro-N-[2-((R)-indan-1-ylamino)-quinolin-6-yl]-benzamide,
4-Fluoro-N-[2-((R)-indan-1-ylamino)-quinolin-6-ylmethyl]-benzamide,
2-((R)-Indan-1-ylamino)-quinoline-6-carboxylic acid 2-methoxy-benzylamide,
(4-Fluoro-phenyl)-[2-((R)-indan-1-ylamino)-quinolin-6-yl]-methanone oxime,
1-[2-((R)-Indan-1-ylamino)-quinolin-6-yl]-3-(2-methyl-2H-pyrazol-3-yl)-urea,
(6-Imidazol-1-yl-quinolin-2-yl)-(R)-indan-1-yl-amine,
1-Benzoyl-3-[2-((R)-indan-1-ylamino)-quinolin-6-yl]-thiourea,
{6-[(4-Fluoro-benzylamino)-methyl]-quinolin-2-yl}-(R)-indan-1-yl-amine,
$N^2$—(R)-Indan-1-yl-$N^6$-pyrimidin-2-yl-quinoline-2,6-diamine,
$N^6$-(4,6-Dimethyl-pyrimidin-2-yl)-$N^2$—(R)-indan-1-yl-quinoline-2,6-diamine,
$N^2$—(R)-Indan-1-yl-$N^6$-(4-methyl-pyrimidin-2-yl)-quinoline-2,6-diamine,
$N^2$—(R)-Indan-1-yl-$N^6$-pyridin-2-yl-quinoline-2,6-diamine,
$N^2$—(R)-Indan-1-yl-$N^6$-(6-methyl-pyridin-2-yl)-quinoline-2,6-diamine, N²—(R)-Indan-1-yl-N⁶-(4-trifluoromethyl-pyrimidin-2-yl)-quinoline-2,6-diamine,
N²—(R)-Indan-1-yl-N⁶-(5-methyl-isoxazol-3-yl)-quinoline-2,6-diamine,
N⁶-(2-tert-Butyl-2H-tetrazol-5-yl)-N²—(R)-indan-1-yl-quinoline-2,6-diamine,
N⁶-(5-Cyclopropyl-[1,3,4]oxadiazol-2-yl)-N²—(R)-indan-1-yl-quinoline-2,6-diamine,
N²—(R)-Indan-1-yl-N⁶-(5-methyl-[1,3,4]oxadiazol-2-yl)-quinoline-2,6-diamine,
N²—(R)-Indan-1-yl-N⁶-(6-trifluoromethyl-pyridin-2-yl)-quinoline-2,6-diamine,
2-{3-[2-((R)-Indan-1-ylamino)-quinolin-6-ylamino]-phenyl}-ethanol,
N²—(R)-Indan-1-yl-N⁶-methyl-N⁶-pyridin-2-yl-quinoline-2,6-diamine,
rac-N²-(7-Methoxy-indan-1-yl)-N⁶-(6-trifluoromethyl-pyridin-2-yl)-quinoline-2,6-diamine,
rac-N²-(7-Methoxy-indan-1-yl)-N⁶-(4-trifluoromethyl-pyrimidin-2-yl)-quinoline-2,6-diamine,
rac-N⁶-(4,6-Dimethyl-pyrimidin-2-yl)-N²-(7-methoxy-indan-1-yl)-quinoline-2,6-diamine,
rac-N²-(7-Methoxy-indan-1-yl)-N⁶-(6-methyl-pyridin-2-yl)-quinoline-2,6-diamine,
rac-N²-(7-Methoxy-indan-1-yl)-N⁶-(5-methyl-isoxazol-3-yl)-quinoline-2,6-diamine,
rac-2-Imidazol-1-yl-N-[2-(7-methoxy-indan-1-ylamino)-quinolin-6-yl]-acetamide,
rac-N²-(5-Fluoro-indan-1-yl)-N⁶-(6-trifluoromethyl-pyridin-2-yl)-quinoline-2,6-diamine,
rac-N²-(5-Fluoro-indan-1-yl)-N⁶-(4-trifluoromethyl-pyrimidin-2-yl)-quinoline-2,6-diamine,
rac-N⁶-(4,6-Dimethyl-pyrimidin-2-yl)-N²-(5-fluoro-indan-1-yl)-quinoline-2,6-diamine,
rac-N²-(5-Fluoro-indan-1-yl)-N⁶-(6-methyl-pyridin-2-yl)-quinoline-2,6-diamine,
rac-N²-(5-Fluoro-indan-1-yl)-N⁶-(5-methyl-isoxazol-3-yl)-quinoline-2,6-diamine,
rac-N²-(4-Methoxy-2,3-dihydro-benzofuran-3-yl)-N⁶-(6-trifluoromethyl-pyridin-2-yl)-quinoline-2,6-diamine,
rac-N²-(4-Methoxy-2,3-dihydro-benzofuran-3-yl)-N⁶-(4-trifluoromethyl-pyrimidin-2-yl)-quinoline-2,6-diamine,
rac-N⁶-(4,6-Dimethyl-pyrimidin-2-yl)-N²-(4-methoxy-2,3-dihydro-benzofuran-3-yl)-quinoline-2,6-diamine,
rac-N²-(4-Methoxy-2,3-dihydro-benzofuran-3-yl)-N⁶-(6-methyl-pyridin-2-yl)-quinoline-2,6-diamine,
rac-N²-(4-Methoxy-2,3-dihydro-benzofuran-3-yl)-N⁶-(5-methyl-isoxazol-3-yl)-quinoline-2,6-diamine,
rac-N-[2-(7-Methoxy-indan-1-ylamino)-quinolin-6-yl]-2-[1,2,4]triazol-4-yl-acetamide, or
rac-N-[2-(7-Methoxy-indan-1-ylamino)-quinolin-6-yl]-2-pyridin-4-yl-acetamide.

The present compounds of formula I

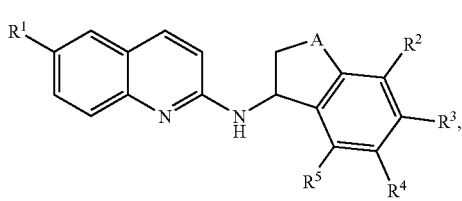

their starting materials, their pharmaceutically acceptable salts, and their optical isomers can be prepared by methods known in the art. For example, a process may be used which comprises one of the following steps:

a) reacting a compound of formula 22

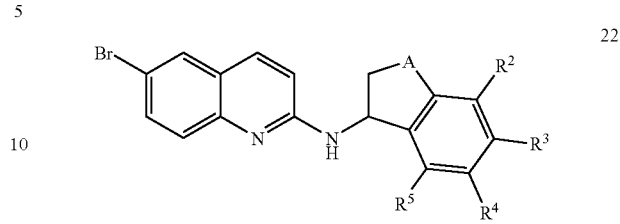

with an aromatic amine of formula Ar¹—NH₂ in a palladium catalyzed substitution reaction of give a compound of formula I wherein R¹ is —NH—Ar¹; or b) reacting a compound of formula 4

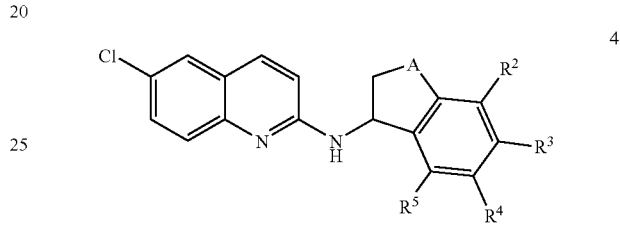

with an amine of formula Ar¹—CH₂—NH₂ and palladium catalyst to give a compound of formula I wherein R¹ is —NH—CH₂—Ar¹; or c) reacting a compound of formula 9

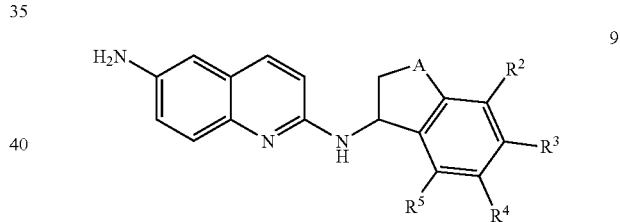

with an amine of formula Ar¹—NH₂ in the presence of triphosgene and NEt₃ to give a compound of formula I wherein R¹ is —NH—C(O)—NH—Ar¹; or d) reacting a compound of formula 9

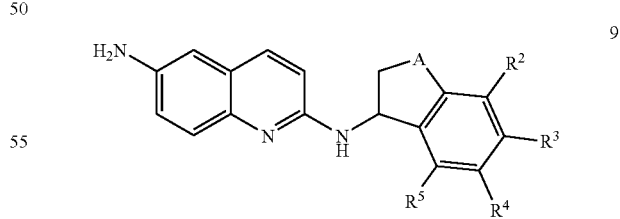

with an isocyanate of formula Ar¹—Y—NCO, wherein Y is a bond or —CHR^f—, with R^f being H or alkyl, to give a compound of formula I wherein R¹ is —NH—C(O)—NH—CHR^f—Ar¹.

As mentioned earlier, the compounds of formula I and their pharmaceutically acceptable addition salts possess valuable pharmaceutical properties. Compounds of the present invention are active on the 5-HT$_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

Test Description

A [$^3$H]LSD radioligand binding assay was used to determine the affinity of the compounds for the recombinant human 5-HT$_{5A}$ receptor, in membranes from transiently (cDNA) expressed 5-HT$_{5A}$ receptors in Human Embryonic Kidney-EBNA (HEK-EBNA) cells. Assay buffer consisted of Tris (50 mM) buffer containing 1 mM EGTA, 10 mM MgCl$_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-1-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. IC$_{50}$ values were calculated using a non-linear curve fitting program and Ki values calculated using the Cheng-Prussoff equation.

The activity of the compounds according to the invention is exemplified in the table 1 below:

| Example | Ki/nM 5-HT$_{5A}$ |
|---------|------------------|
| 2 | 92.4 |
| 4 | 9.8 |
| 9 | 176.3 |
| 11 | 9.4 |
| 12 | 16.6 |
| 13 | 7.6 |
| 14 | 36.4 |
| 15 | 33.7 |
| 16 | 4.9 |
| 17 | 7.6 |
| 18 | 9.0 |
| 19 | 6.5 |
| 20 | 7.8 |
| 21 | 6.3 |
| 22 | 21.9 |
| 23 | 25.6 |
| 25 | 4.2 |
| 27 | 9.8 |
| 28 | 36.7 |
| 29 | 16.5 |
| 31 | 16.4 |
| 33 | 18.2 |
| 40 | 29.6 |
| 41 | 25.8 |
| 42 | 25.8 |
| 45 | 10.6 |
| 47 | 20.0 |
| 50 | 72.5 |
| 54 | 140.9 |
| 55 | 280.9 |
| 56 | 141.2 |
| 58 | 20.3 |
| 61 | 421.6 |
| 63 | 389.8 |
| 64 | 348.4 |
| 66 | 23.2 |
| 67 | 15.7 |
| 68 | 20.0 |
| 69 | 20.4 |
| 72 | 7.7 |
| 73 | 11.0 |
| 74 | 8.7 |
| 75 | 25.9 |
| 76 | 24.8 |
| 77 | 21.2 |
| 80 | 24.1 |
| 83 | 9.6 |
| 85 | 224.7 |
| 91 | 5.4 |
| 92 | 4.3 |
| 93 | 3.4 |
| 94 | 3.4 |
| 95 | 3.5 |
| 100 | 21.2 |
| 102 | 19.1 |
| 103 | 13.7 |
| 104 | 9.0 |
| 105 | 6.8 |
| 106 | 7.3 |
| 109 | 26.1 |
| 110 | 11.8 |
| 111 | 9.1 |
| 112 | 8.0 |
| 113 | 14.4 |
| 114 | 26.9 |
| 115 | 15.0 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment of anxiety, depression, sleep disorders and schizophrenia.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| | Tablet Formulation (Wet Granulation) | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | Capsule Formulation | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

Preparation of the compounds of present invention:

Compounds of formula I may be prepared as shown in the following description:

In the following Routes 1 to 17, the symbol $R^4$ means a moiety of

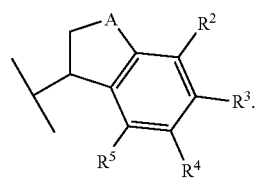

Route 1 Described in Example 1

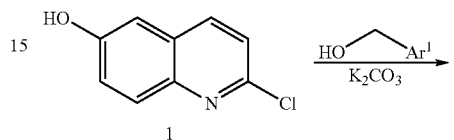

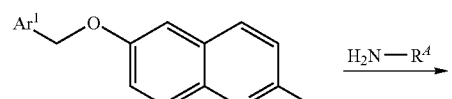

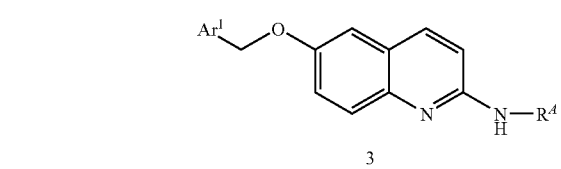

2-Chloro-6-hydroxy-quinoline (1, CAS-no: 577967-89-6) is reacted with benzylic alcohols in the presence of a base such as potassium carbonate to the intermediate 2, which is subsequently condensed under thermal conditions with an amine to yield the final products 3. $Ar^1$ is as described herein.

Route 2 Described in Example 4

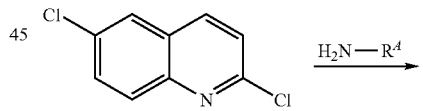

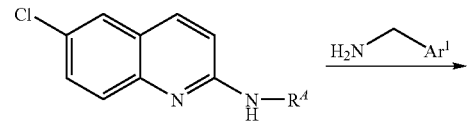

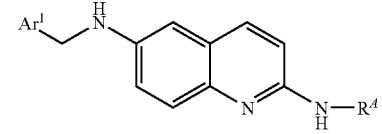

2,6-Dichloroquinoline (4) is reacted with 2 equivalents of an amine ($R^4NH_2$) without solvent. Intermediate 5 is reacted with an amine ($Ar^1CH_2NH_2$) in a palladium catalyzed substitution reaction. $Ar^1$ is as described herein.

Route 3 Described in Example 11

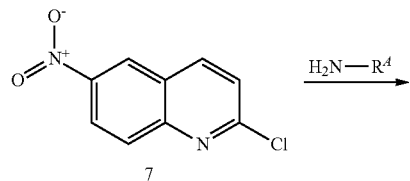

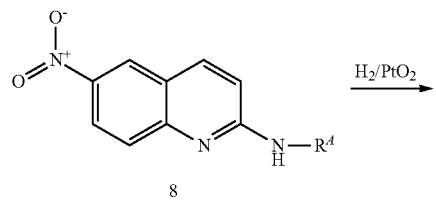

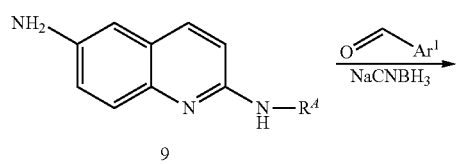

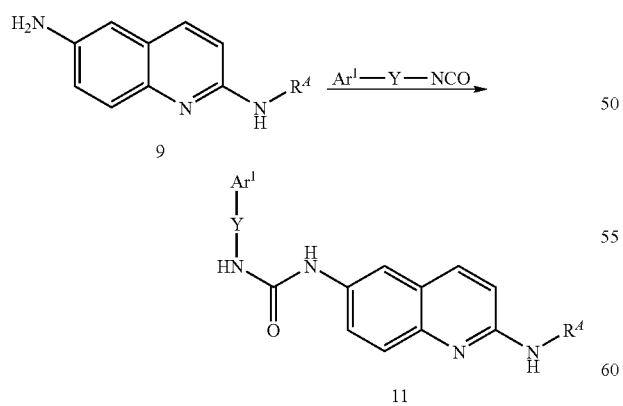

2-Chloro-6-nitro-quinoline (7, CAS-no: 29969-57-1) is reacted with an amine to intermediate 8 which is reduced under an atmosphere of hydrogen in presence of platinum oxide. Amine 9 is then reacted with an aldehyde in presence of cyanoborohydrid to yield the final product 10. Ar¹ is as described herein.

Route 4 Described in Example 16

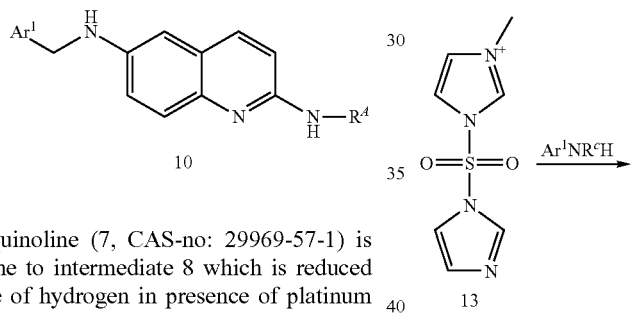

6-Amino-quinoline 9 is treated with an isocyanate of formula Ar¹—Y—NCO wherein Y is a bond or —CHR$^f$— with R$^f$ being H or alkyl, to yield a urea derivative of formula 11. Ar¹ is as described herein.

Route 5 Described in Example 33

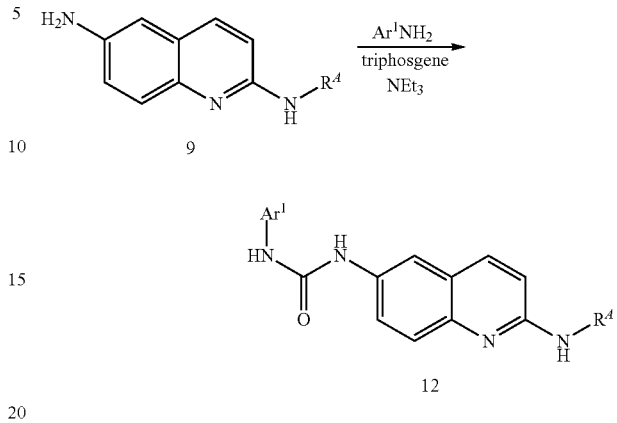

6-Amino-quinoline 9 is treated with Ar¹NH₂ in the presence of triphosgene and a base such as triethylamine to yield urea derivatives 12. Ar¹ is as described herein.

Route 6 Described in Example 37

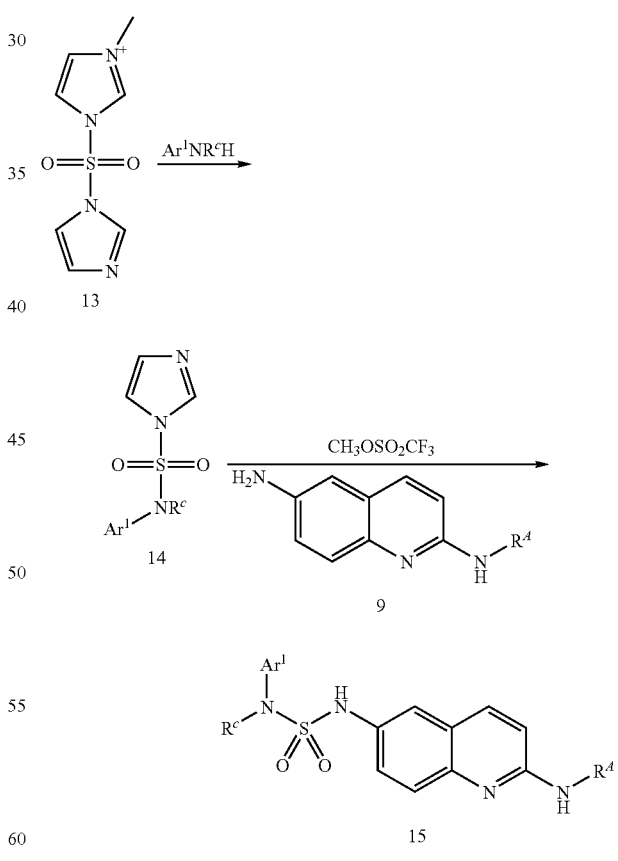

1H-Imidazolium, 3-(1H-imidazol-1-ylsulfonyl)-1-methyl-, trifluoromethanesulfonate (13, CAS no: 489471-57-0) is treated with Ar¹NR$^c$H (wherein Ar¹ is as described herein and R$^c$ is H or alkyl), then with methyl triflate and subsequently with intermediate 9 to yield sulfamide 15.

Route 7 Described in Example 47

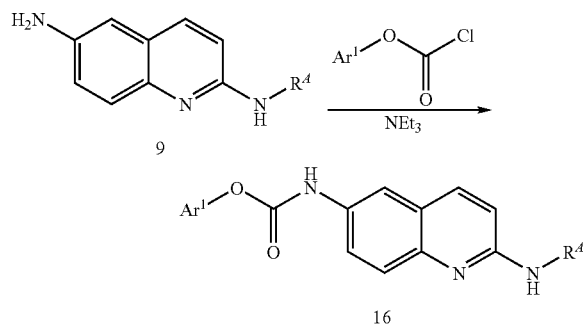

6-Amino-quinoline 9 is treated with a chloroformate Ar¹OC(O)Cl in toluene and triethyl amine to yield carbamate derivative 16. Ar¹ is as described herein.

Route 8 Described in Example 49

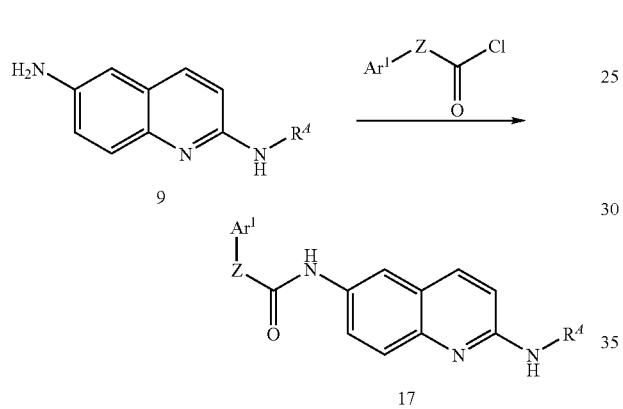

6-Amino-quinoline 9 is treated with an acid chloride Ar¹—Z—C(O)Cl in triethyl amine and toluene to yield carboxamide derivative 17. Thereby, Z is —$CH_2$— or a bond and Ar¹ is as described herein.

Route 9 Described in Example 6 and 51

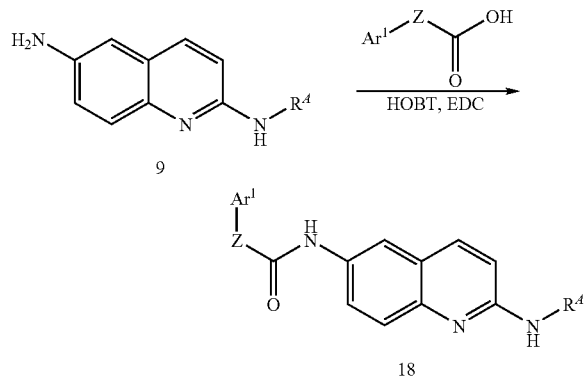

6-Amino-quinoline 9 is treated with a carboxylic acid Ar¹—Z—COOH in the presence of an amide coupling reagent such as 2-(1H-benzotriazole-1-yl)-1,1,3,3-tetramethyluronium tetrafluoroborate (HOBt) and N,N-diisopropyl ethyl amine with or without 1-(3-dimethylaminopropyl)-3-ethylcarbodiimide hydrochloride (EDC) to yield carboxamide derivative 18. Thereby, Z is —$CH_2$— or a bond and Ar¹ is as described herein.

Route 10 Described in Example 52

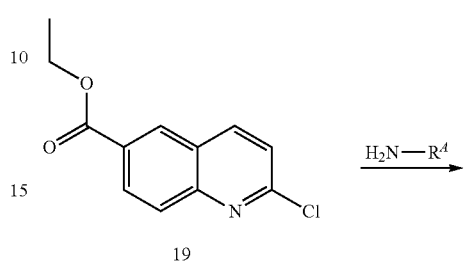

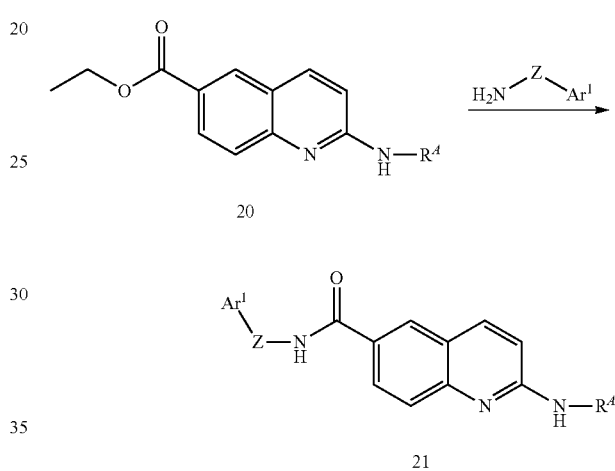

2-Chloro-quinoline-6-carboxylic acid ethyl ester [CAS-no 29969-56-0] is reacted with an amine of formula $R^4$—$NH_2$ to yield intermediate 20. Further, an amine of formula Ar¹—Z—$NH_2$ (wherein Ar¹ is as described herein and Z is either —$CH_2$— or a bond) is treated with trimethylaluminium and subsequently reacted with intermediate 20 to yield the product of formula 21.

Route 11 Described in Example 53

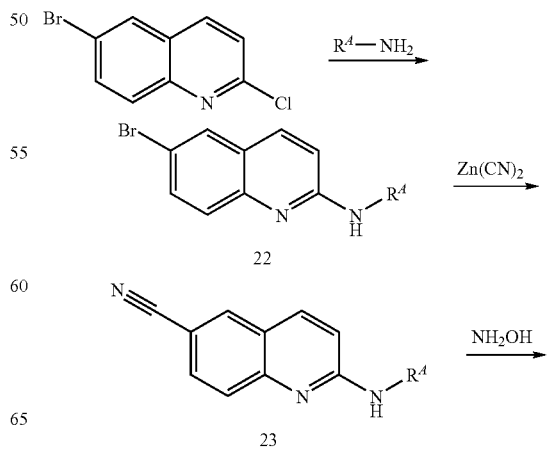

19

-continued

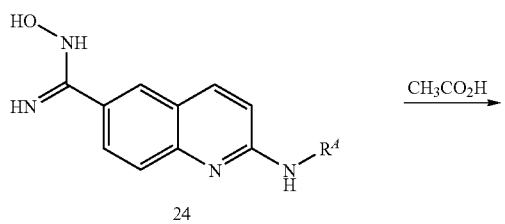

24

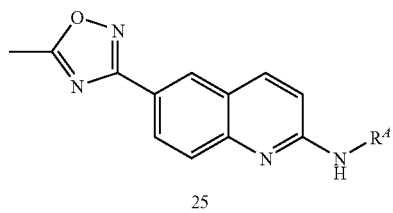

25

Commercially available 6-bromo-2-chloro-quinoline is heated with an amine of formula R$^A$—NH$_2$ to result in intermediate 22, which is subsequently reacted with zinc cyanide in a palladium catalyzed substitution reaction. Reaction of cyano derivatives 23 with hydroxylamine to the corresponding amidoximes 24. Formation of the methyl-oxadiazole derivatives 25 with acetic acid, 1-hydroxy-benzotriazole and N-(3-dimethylaminopropyl)-N'-ethyl-carbodiimid-hydrochloride.

Route 12 Described in Example 54

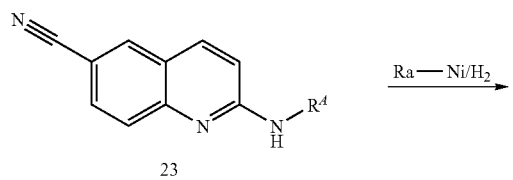

23

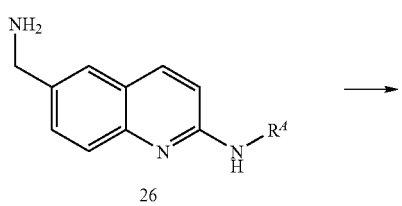

26

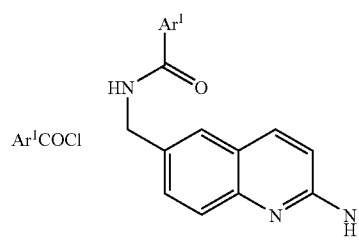

27

The cyano group in compound 23 is reduced by hydrogenation to amine 26, which is then reacted with a compound of formula Ar$^1$COCl.

20

Route 13 Described in Example 56

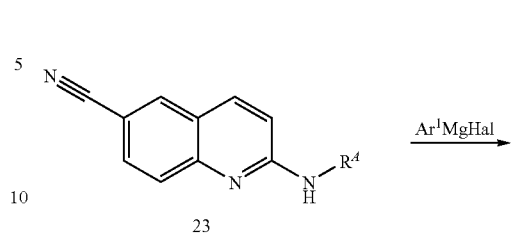

23

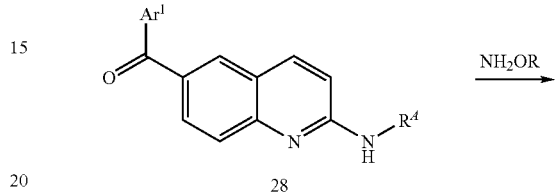

28

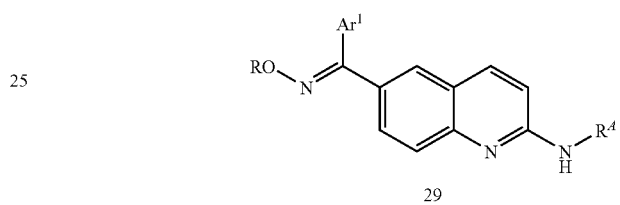

29

Reaction of cyano derivative 23 with an aryl Grignard reagent (Ar$^1$MgHal). Reaction of ketone 28 with hydroxylamine to the corresponding oxime 29.

Route 14 Described in Example 63

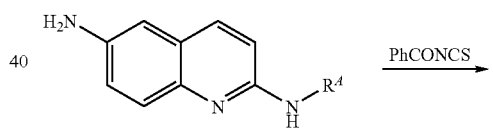

9

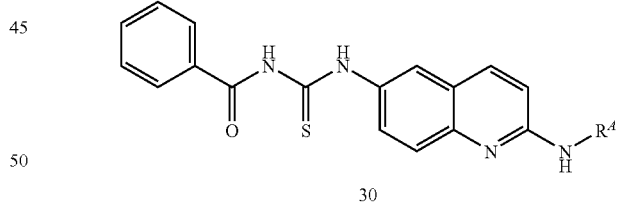

30

6-Amino-quinoline 9 is treated with benzoyl-isothiocyanate to yield thiourea 30.

Route 15 Described in Example 64

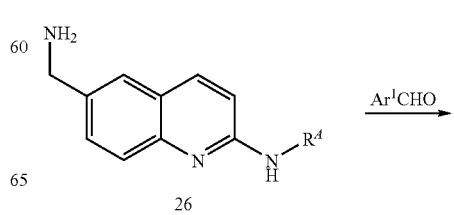

26

21
-continued

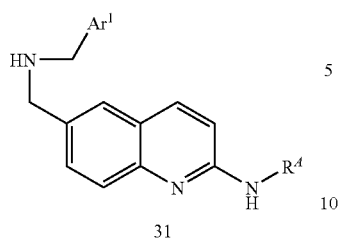

Reductive amination of benzaldehydes (Ar¹CHO) with amines 26.
Route 16 Described in Example 65

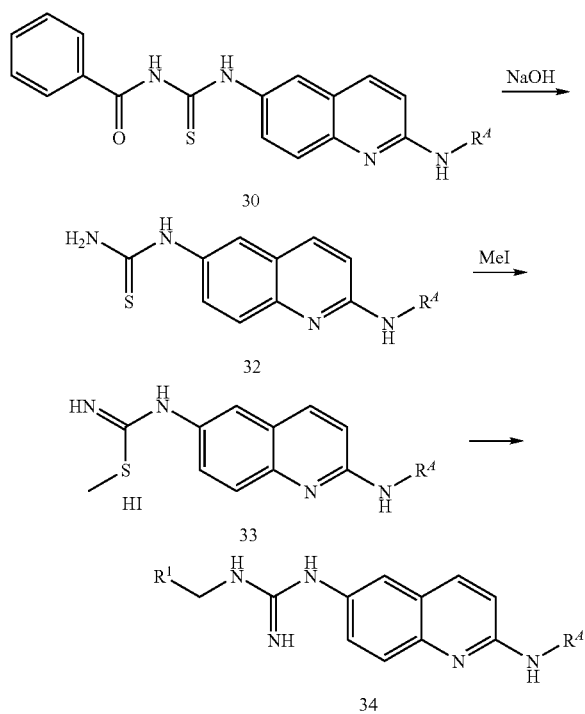

Intermediate 30 is treated with sodium hydroxide to yield thiourea 32 which is treated with methyl iodide to yield the intermediate 33. Intermediate 33 is reacted with an amine to yield guanidine 34.
Route 17 Described in Example 66

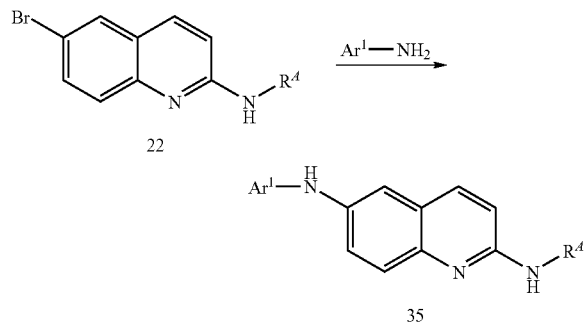

Compound 22 (synthesized according to Route 11) is reacted with an aromatic amine in a palladium catalyzed substitution reaction to give a product of formula 35, wherein Ar¹ is as defined herein.

EXAMPLES

Example 1

[6-(4-Fluoro-benzyloxy)-quinolin-2-yl]-(R)-indan-1-yl-amine

Step A: To a stirred solution of 2-chloro-6-hydroxy-quinoline (0.6 g, 3.0 mmol) in acetone (15 ml) potassium carbonate (0.55 g, 4.0 mmol) and 4-fluorobenzylbromide (0.76 g, 4.0 mmol) were added at ambient temperature. Then the reaction mixture was heated to reflux for 3 h. Upon cooling to ambient temperature water was added and the whole mixture extracted twice with ethyl acetate. The combined organic phases were dried on sodium sulfate, filtered and evaporated. Purification of the residue by flash chromatography on silica gel (heptane, ethyl acetate 1:0=>1:4) yielded 2-chloro-6-(4-fluoro-benzyloxy)-quinoline as a white solid (0.19 g, 20%), MS 288.8 [(M+H)⁺].

Step B: A stirred mixture of 2-chloro-6-(4-fluoro-benzyloxy)-quinoline (0.08 g, 0.4 mmol) and (R)-1-aminoindane (0.107 g, 1.00 mmol) was heated in a sealed tube for 20 h at 130° C. Purification by flash chromatography on silica gel (ethyl acetate in heptane, 0→80%) yielded the title compound as a dark oil (9 mg, 8%), MS 385.6 [(M+H)⁺].

Example 2

(R)-Indan-1-yl-[6-(3-methoxy-benzyloxy)-quinolin-2-yl]-amine

Step A: To a stirred solution of 2-chloro-6-hydroxy-quinoline (0.6 g, 3.0 mmol) in aceton (15 ml) potassium carbonate (0.55 g, 4.0 mmol) and 3-methoxybenzylbromide (0.8 g, 4.0 mmol) were added at ambient temperature. Then the reaction mixture was heated to reflux for 3 h. Upon cooling to ambient temperature water was added and the whole mixture extracted twice with ethyl acetate. The combined organic phases were dried on sodium sulfate, filtered and evaporated. Purification of the residue by flash chromatography on silica gel (heptane, ethyl acetate 1:0=>1:4) yielded 2-chloro-6-(3-methoxy-benzyloxy)-quinoline as a white solid (0.4 g, 40%), MS 300.8 [(M+H)⁺].

Step B: A stirred mixture of 2-chloro-6-(3-methoxy-benzyloxy)-quinoline (0.08 g, 0.4 mmol) and (R)-1-aminoindane (0.107 g, 1.00 mmol) was heated in a sealed tube for 20 h at 130° C. Purification by flash chromatography on silica gel (ethyl acetate in heptane, 0=>100%) yielded the title compound as a dark oil (11 mg, 10%), MS 397.5 [(M+H)⁺].

Example 3

(R)-Indan-1-yl-[6-(pyridin-3-ylmethoxy)-quinolin-2-yl]-amine

The title compound, MS: m/e=368.6 (M+H⁺), was prepared in accordance with the general method of example 1 from 2-chloro-6-hydroxy-quinoline, (R)-1-aminoindane and 3-(brommethyl)pyridine-HBr.

Example 4

N²—(R)-Indan-1-yl-N⁶-pyridin-3-ylmethyl-quinoline-2,6-diamine

Step A: A stirred mixture of 2,6-dichloro-quinoline (4.8 g, 24 mmol) and (R)-1-aminoindane (6.5 g, 48 mmol) was heated in a sealed tube for 16 h at 125° C. Purification by flash chromatography on silica gel (ethyl acetate/heptane) yielded (6-chloro-quinolin-2-yl)-(R)-indan-1-yl-amine as a yellow solid (2.4 g, 34%), MS 295.1 [(M+H)⁺].

Step B: (6-Chloro-quinolin-2-yl)-(R)-indan-1-yl-amine (200 mg, 0.678 mmol) was dissolved in 2.5 mL toluene and 0.5 mL t-butanol. Argon was bubbled through the solution for 2 minutes to remove oxygen. 3-Picolylamine (220 mg, 2.04 mmol), sodium tert.-butylate (156 mg, 1.63 mmol), 2-dicyclohexylphosphino-2',4',6'-triisopropylbiphenyl (65 mg, 0.14 mmol) and palladium acetate (15 mg, 0.07 mmol) were added. The reaction mixture was stirred in a sealed tube at 130° C. overnight. The solvent was evaporated and the residue purified by flash chromatography on silica gel (dichloromethane/methanol 100:0=>95:50 gradient). The title compound was obtained as a yellow foam (39 mg, 16%), MS: m/e=367.4 (M+H⁺).

Example 5

N²—(R)-Indan-1-yl-N⁶-(1-methyl-1H-imidazol-2-ylmethyl)-quinoline-2,6-diamine The title compound, MS: m/e=370.0 (M+H⁺), was prepared in accordance with the general method of example 4 from 2,6-dichloro-quinoline, (R)-1-aminoindane and 1-methyl-2-aminomethylimidazole.

Example 6 rac-N-[2-(5-Fluoro-indan-1-ylamino)-quinolin-6-yl]-2-pyridin-3-yl-acetamide

Step A: 2-Chloro-6-nitro-quinoline (2.7 g, 13 mmol) and rac-5-fluoro-indan-1-ylamine (CAS 148960-33-2, 3.9 g, 26 mmol) were heated at 130° C. for 24 h. The reaction mixture was purified by flash chromatography on silica gel (dichloromethane). rac-(5-Fluoro-indan-1-yl)-(6-nitro-quinolin-2-yl)-amine was obtained as a yellow solid (2.99 g, 71%), MS: m/e=324.4 (M+H⁺).

Step B: rac-(5-Fluoro-indan-1-yl)-(6-nitro-quinolin-2-yl)-amine (1.1 g, 3.4 mmol) were dissolved in ethyl acetate (60 ml). Upon addition of Pd/C (10%) the reaction mixture was stirred for 2 h at ambient temperature under an atmosphere of hydrogen. Then the catalyst was filtered off, the filter washed with ethyl acetate and the filtrate evaporated. rac-N²-(5-Fluoro-indan-1-yl)-quinoline-2,6-diamine was obtained as a yellow foam (1.0 g, 99%); MS: m/e=294.3 (M+H⁺).

Step C: 3-Pyridyl-acetic acid (112 mg, 0.82 mmol), N,N-diisopropyl ethyl amine (308 mg, 2.4 mmol) and 2-(1H-benzotriazole-1-yl)-1,1,3,3-tetramethyluronium tetrafluoroborate (350 mg, 1.1 mmol) were dissolved in dichloromethane (20 mL) and dimethylformamide (5 mL). The reaction mixture was stirred at room temperature for 30 minutes. rac-N²-(5-Fluoro-indan-1-yl)-quinoline-2,6-diamine (2000 mg, 0.68 mmol) was added and stirred was continued overnight. The reaction mixture was diluted with water and extracted with dichloromethane (3×). The combined organic phases were dried over sodium sulfate and evaporated. The crude product was recrystallized with dichloromethane. The title compound (144 mg, 51%) was obtained as an off-white solid; MS: m/e=413.4 (M+H⁺).

Example 7

N²—(R)-Indan-1-yl-N⁶-(3-methyl-3H-imidazol-4-ylmethyl)-quinoline-2,6-diamine The title compound, MS: m/e=370.6 (M+H⁺), was prepared in accordance with the general method of example 4 from 2,6-dichloro-quinoline, (R)-1-aminoindane and 1-methyl-4-aminomethylimidazole.

Example 8

N²—(R)-Indan-1-yl-N⁶-(3-methanesulfonyl-benzyl)-quinoline-2,6-diamine

The title compound, MS: m/e=444.8 (M+H⁺), was prepared in accordance with the general method of example 4 from 2,6-dichloro-quinoline, (R)-1-aminoindane and 3-(methylsulfonyl)benzylamin.

Example 9

N⁶-(3-Imidazol-1-yl-propyl)-N²—(R)-indan-1-yl-quinoline-2,6-diamine

The title compound, MS: m/e=384.6 (M+H⁺), was prepared in accordance with the general method of example 4 from 2,6-dichloro-quinoline, (R)-1-aminoindane and N-(3-aminopropyl)imidazole.

Example 10

N²—(R)-Indan-1-yl-N⁶-(1-methyl-1H-imidazol-4-ylmethyl)-quinoline-2,6-diamine The title compound, MS: m/e=370.6 (M+H⁺), was prepared in accordance with the general method of example 4 from 2,6-dichloro-quinoline, (R)-1-aminoindane and 1-methyl-1H-imidazol-4-yl-methylamin.

Example 11

N²—(R)-Indan-1-yl-N⁶-(1-H-indol-4-ylmethyl)-quinoline-2,6-diamine

Step A: A stirred mixture of 2-chloro-6-nitro-quinoline (2.2 g, 11 mmol) and (R)-1-aminoindane (2.8 g, 21 mmol) was heated in a sealed tube for 20 h at 125° C. Purification by flash chromatography on silica gel (ethyl acetate/heptane 0:1=>3:7) yielded (6-nitro-quinolin-2-yl)-(R)-indan-1-yl-amine as a brownish solid (1.5 g, 47%), MS 306.5 [(M+H)⁺].

Step B: (6-Nitro-quinolin-2-yl)-(R)-indan-1-yl-amine (0.37 g, 1.2 mmol) was dissolved in ethanol (15 mL). Platinum oxide hydrate (9 mg) was added and the mixture stirred for 4 h at ambient temperature under an atmosphere of hydrogen. The reaction mixture was filtered and evaporated and the residue was subjected to column chromatography (silica gel, heptane, ethyl acetate 1:0=>6:4). (6-Amino-quinolin-2-yl)-(R)-indan-1-yl-amine was isolated as a yellow foam (0.22 g, 66%); MS 276.5 [(M+H)⁺].

Step C: (6-Amino-quinolin-2-yl)-(R)-indan-1-yl-amine (0.10 g, 0.36 mmol), indol-4-carboxaldehyde (0.063 g, 0.44 mmol) and acetic acid (0.06 mL) were dissolved in methanol (3 mL). After 3 h of stirring at ambient temperature NaBH₃CN (0.057 g, 0.91 mmol) was added and the reaction mixture stirred for 16 h at ambient temperature. Saturated sodium bicarbonate solution was added then and the aqueous phase extracted with ethyl acetate (3×20 mL). The combined organic phases were dried over sodium sulfate, filtered and the filtrate was evaporated. The residual yellow oil was subjected to column chromatography (silica gel, heptane, ethyl acetate; 9:1=>1:2) to yield the title compound as a yellow foam (34 mg, 23%); MS 405.7 [(M+H)⁺].

Example 12

N⁶-(1H-Imidazol-2-ylmethyl)-N²—(R)-indan-1-yl-quinoline-2,6-diamine

The title compound, MS: m/e=356.8 (M+H⁺), was prepared in accordance with the general method of example 11 from 2-chloro-6-nitro-quinoline, (R)-1-aminoindane and imidazol-2-carboxaldehyde.

Example 13

N²—(R)-Indan-1-yl-N⁶-thiazol-2-ylmethyl-quinoline-2,6-diamine

The title compound, MS: m/e=373.8 (M+H⁺), was prepared in accordance with the general method of example 11 from 2-chloro-6-nitro-quinoline, (R)-1-aminoindane and 2-formylthiazol.

Example 14

4-Fluoro-N-[2-((R)-indan-1-ylamino)-quinolin-6-yl]-benzenesulfonamide (6-Amino-quinolin-2-yl)-(R)-indan-1-yl-amine (0.05 g, 0.18 mmol) and 4-fluoro-benzenesulfonyl chloride (0.035 g, 0.18 mmol) were dissolved in pyridine (1 mL). The reaction mixture was stirred for 16 h at ambient temperature. Saturated sodium bicarbonate solution was added then and the aqueous phase extracted with ethyl acetate (3×10 mL). The combined organic phases were dried over sodium sulfate, filtered and the filtrate was evaporated. The residual oil was subjected to column chromatography (silica gel, heptane, ethyl acetate; 9:1=>1:1) to yield the title compound as a brown solid (5 mg, 6%); MS 434.7 [(M+H)⁺].

Example 15

N²—(R)-Indan-1-yl-N⁶-pyridin-4-ylmethyl-quinoline-2,6-diamine

The title compound, MS: m/e=367.6 (M+H⁺), was prepared in accordance with the general method of example 4 from 2,6-dichloro-quinoline, (R)-1-aminoindane and 4-(aminomethyl)pyridine.

Example 16

1-[2-((R)-Indan-1-ylamino)-quinolin-6-yl]-3-phenyl-urea (R)—N-2-Indan-1-yl-quinoline-2,6-diamine (0.10 g, 0.36 mmol) was dissolved in toluene (3 ml). Phenyl isocyanate (0.043 mL, 0.36 mmol) was added and the reaction mixture was stirred at 110° C. for 2 h. Upon cooling to room temperature a precipitation formed which was filtered off and washed twice with dichloromethane. After trying the title compound was obtained as a grey solid (86 mg, 60%); MS: m/e=395.6 (M+H⁺).

Example 17

N²—(R)-Indan-1-yl-N⁶-(5-methyl-3-H-imidazol-4-ylmethyl)-quinoline-2,6-diamine

The title compound, MS: m/e=370.7 (M+H⁺), was prepared in accordance with the general method of example 11 from 2-chloro-6-nitro-quinoline, (R)-1-aminoindane and 5-methyl-3H-imidazole-4-carboxaldehyde.

Example 18

N²—(R)-Indan-1-yl-N⁶-(1-H-pyrazol-3-ylmethyl)-quinoline-2,6-diamine

The title compound, MS: m/e=356.6 (M+H⁺), was prepared in accordance with the general method of example 11 from 2-chloro-6-nitro-quinoline, (R)-1-aminoindane and 1H-pyrazole-3-carboxaldehyde.

Example 19

1-(4-Fluoro-phenyl)-3-[2-((R)-indan-1-ylamino)-quinolin-6-yl]-urea

The title compound, MS: m/e=413.7 (M+H⁺), was prepared in accordance with the general method 4 of example 16 from (R)—N²-indan-1-yl-quinoline-2,6-diamine and 1-fluoro-4-isocyanato-benzene.

Example 20

1-(3-Fluoro-phenyl)-3-[2-((R)-indan-1-ylamino)-quinolin-6-yl]-urea

The title compound, MS: m/e=413.7 (M+H⁺), was prepared in accordance with the general method 4 of example 16 from (R)—N²-indan-1-yl-quinoline-2,6-diamine and 1-fluoro-3-isocyanato-benzene.

Example 21

1-[2-((R)-Indan-1-ylamino)-quinolin-6-yl]-3-(4-methoxy-phenyl)-urea

The title compound, MS: m/e=425.7 (M+H⁺), was prepared in accordance with the general method 4 of example 16 from (R)—N²-indan-1-yl-quinoline-2,6-diamine and 4-methoxyphenyl-isocyanate.

Example 22

1-[2-((R)-Indan-1-ylamino)-quinolin-6-yl]-3-(3-methoxy-phenyl)-urea

The title compound, MS: m/e=425.7 (M+H⁺), was prepared in accordance with the general method 4 of example 16 from (R)—N²-indan-1-yl-quinoline-2,6-diamine and 3-methoxyphenyl-isocyanate.

Example 23

1-[2-((R)-Indan-1-ylamino)-quinolin-6-yl]-3-(2-methoxy-phenyl)-urea

The title compound, MS: m/e=425.7 (M+H$^+$), was prepared in accordance with the general method 4 of example 16 from (R)—N$^2$-indan-1-yl-quinoline-2,6-diamine and 2-methoxyphenyl-isocyanate.

Example 24

1-Allyl-1-[2-((R)-indan-1-ylamino)-quinolin-6-yl]-3-(4-methoxy-phenyl)-urea

Step A: (6-Iodo-quinolin-2-yl)-(R)-indan-1-yl-amine (8.45 g, 0.022 mol) was dissolved in dioxane (50 mL). Argon was bubbled through the solution for 2 minutes to remove oxygen. Allylamine (4.93 ml, 0.066 mol), sodium tert.-butylate (3.57 g, 0.034 mol), palladium acetate (246 mg) and X-phos (1.56 g, 0.003 mol) were added. The reaction mixture was stirred in a sealed tube at 100° C. for 2.5 h. The solvent was evaporated and the residue purified by flash chromatography on silica gel (ethyl acetate/heptane 50:50=>100:0 gradient). N$^6$-Allyl-N$^2$—(R)-indan-1-yl-quinoline-2,6-diamine was obtained as a yellow oil (5.19 g, 71.5%), MS: m/e=316.7 (M+H$^+$).

Step B: The title compound, MS: m/e=465.7 (M+H$^+$), was prepared in accordance with the general method 4 of example 16 from (N-6-allyl-N$^2$—(R)-indan-1-yl-quinoline-2,6-diamine and 4-methoxyphenyl-isocyanate.

Example 25

1-(2-Fluoro-phenyl)-3-[2-((R)-indan-1-ylamino)-quinolin-6-yl]-urea

The title compound, MS: m/e=413.7 (M+H$^+$), was prepared in accordance with the general method 4 of example 16 from (R)—N$^2$-indan-1-yl-quinoline-2,6-diamine and 2-fluorophenyl-isocyanate.

Example 26

3-[2-((R)-Indan-1-ylamino)-quinolin-6-yl]-1-methyl-1-phenyl-urea

The title compound, MS: m/e=409.7 (M+H$^+$), was prepared in accordance with the general method 4 of example 16 from (R)—N$^2$-indan-1-yl-quinoline-2,6-diamine, triethylamine and N-methyl-N-phenylcarbamoyl chloride.

Example 27

1-[2-((R)-Indan-1-ylamino)-quinolin-6-yl]-3-((R)-1-phenyl-ethyl)-urea

The title compound, MS: m/e=423.7 (M+H$^+$), was prepared in accordance with the general method 4 of example 16 from (R)—N$^2$-indan-1-yl-quinoline-2,6-diamine and R(+)-1-phenylethyl isocyanate.

Example 28

1-[2-((R)-Indan-1-ylamino)-quinolin-6-yl]-3-((S)-1-phenyl-ethyl)-urea

The title compound, MS: m/e=423.7 (M+H$^+$), was prepared in accordance with the general method 4 of example 16 from (R)—N$^2$-indan-1-yl-quinoline-2,6-diamine and S(−)-1-phenylethyl isocyanate.

Example 29

1-[2-((R)-Indan-1-ylamino)-quinolin-6-yl]-3-(4-methoxy-benzyl)-urea

The title compound, MS: m/e=439.7 (M+H$^+$), was prepared in accordance with the general method 4 of example 16 from (R)—N$^2$-indan-1-yl-quinoline-2,6-diamine and 4-methoxybenzyl isocyanate.

Example 30

1-[2-((R)-Indan-1-ylamino)-quinolin-6-yl]-3-(4-trifluoromethyl-phenyl)-urea

The title compound, MS: m/e=463.6 (M+H$^+$), was prepared in accordance with the general method 4 of example 16 from (R)—N$^2$-indan-1-yl-quinoline-2,6-diamine and 4-(trifluoromethyl)phenyl isocyanate.

Example 31

1-(6-Chloro-pyridin-3-yl)-3-[2-((R)-indan-1-ylamino)-quinolin-6-yl]-urea

The title compound, MS: m/e=431.0 (M+H$^+$), was prepared in accordance with the general method 4 of example 16 from (R)—N$^2$-indan-1-yl-quinoline-2,6-diamine and 2-chloro-5-isocyanatopyridine.

Example 32

1-[2-((R)-Indan-1-ylamino)-quinolin-6-yl]-3-(4-methoxy-phenyl)-1-propyl-urea Allyl-1-[2-((R)-indan-1-ylamino)-quinolin-6-yl]-3-(4-methoxy-phenyl)-urea (38 mg, 0.08 mmol) was dissolved in methanol (2 mL). Pd/C (10 mg, 10%) was added and the reaction mixture was stirred under an atmosphere of hydrogen at ambient temperature for 1 h. Then the mixture was filtered, the filter washed with methanol and the filtrate concentrated and dried under high vacuum. The title compound (12 mg, 32%) was obtained as a yellow solid; MS: (ISP) 467.8 [(M+H)$^+$].

Example 33

1-(2-Chloro-pyridin-4-yl)-3-[2-((R)-indan-1-ylamino)-quinolin-6-yl]-urea (R)—N$^2$-indan-1-yl-quinoline-2,6-diamine (100 mg, 0.36 mmol) and triethylamine (55 μL, 0.8 mmol) were dissolved in THF (5 mL). At 0° C. triphosgene (48.5 mg, 0.16 mmol) was added and the reaction mixture stirred for 5 h at reflux. Then at ambient temperature 4-amino-2-chloropyridine (63 mg, 0.36 mmol) and triethylamine (55 μL, 0.8 mmol) were added. After stirring the reaction mixture at 50° C. over night water was added (20 mL) and the mixture extracted with ethyl acetate (3×15 mL). The combined organic phases were dried on sodium sulfate, filtered and evaporated. The residue was subjected to column chromatography (silica gel; methylene chloride, methanol 100:0=>90:10) to yield the title compound (68 mg, 44%) as a yellow solid; MS: (ISP) 431.0 [(M+H)$^+$].

Example 34

1-(2-Bromo-6-methyl-pyridin-4-yl)-3-[2-((R)-indan-1-ylamino)-quinolin-6-yl]-urea The title compound, MS: m/e=489.5 (M+H$^+$), was prepared in accordance with the general method 5 of example 34 from (R)—N$^2$-indan-1-yl-quinoline-2,6-diamine and 2-bromo-6-methyl-pyridin-4-ylamine.

Example 35

1-(2-Bromo-3-methyl-pyridin-4-yl)-3-[2-((R)-indan-1-ylamino)-quinolin-6-yl]-urea The title compound, MS: m/e=489.5 (M+H$^+$), was prepared in accordance with the general method 5 of example 34 from (R)—N$^2$-indan-1-yl-quinoline-2,6-diamine and 2-bromo-3-methyl-pyridin-4-ylamine.

Example 36

1-[2-((R)-Indan-1-ylamino)-quinolin-6-yl]-3-(2-morpholin-4-yl-pyridin-4-yl)-urea The title compound, MS: m/e=481.6 (M+H$^+$), was prepared in accordance with the general method 4 of example 16 from (R)—N$^2$-indan-1-yl-quinoline-2,6-diamine and 4-(4-isocyanatopyrid-2-yl)-morpholine.

Example 37

N'-{2-[(1R)-2,3-dihydro-1H-inden-1-ylamino]quinolin-6-yl}-N-(4-methoxyphenyl)-N-methylsulfamide Step A: 3-(1H-Imidazol-1-ylsulfonyl)-1-methyl-1H-imidazolium trifluoromethanesulfonate (0.635 g, 1.75 mmol) was dissolved in acetonitrile (5 mL) and treated with N-methyl-p-anisidin (0.2 g, 1.45 mmol) and stirred for 16 h at ambient temperature. The solvent was removed and the residue subjected to column chromatography (silica gel, heptan, ethyl acetate 9:1, 4:1, 1:1) to yield imidazole-1-sulfonic acid 4-methoxy-phenyl)-methyl-amide (0.23 g, 59%) as a yellow oil; MS: m/e=268.5 (M+H$^+$).
Step B: Imidazole-1-sulfonic acid 4-methoxy-phenyl)-methyl-amide (0.20 g, 0.75 mmol) were dissolved in methylene chloride (4 mL) and methyl triflate (0.2 mL, 0.82 mmol) was added drop-wise at 0° C. After stirring for 2 h at 0° C. the solvent was evaporated to yield trifluoro-methanesulfonate3-[(4-methoxy-phenyl)-methyl-sulfamoyl]-1-methyl-3(H)-imidazol-1-ium; (0.30 g, 93%) as a brown oil; MS: m/e=283.2 (M$^+$).
Step C: Trifluoro-methanesulfonate3-[(4-methoxy-phenyl)-methyl-sulfamoyl]-1-methyl-3(H)-imidazol-1-ium (0.188 g, 0.436 mmol) and (R)—N$^2$-indan-1-yl-quinoline-2,6-diamine (0.10 g, 0.36 mmol) were dissolved in acetonitrile (2 mL) and stirred for 16 h at 80° C. The solvent was removed and the residue subjected to column chromatography (silica gel, heptan, ethyl acetate 9:1, 4:1, 1:1) to yield the title compound (0.015 g, 9%) as a yellow solid; MS: m/e=475.7 (M+H$^+$).

Example 38

N'-{2-[(1R)-2,3-dihydro-1H-inden-1-ylamino]quinolin-6-yl}-N-methyl-N-(4-methylphenyl)sulfamide The title compound, MS: m/e=459.7 (M+H$^+$), was prepared in accordance with the general method 6 of example 37 from (R)—N$^2$-indan-1-yl-quinoline-2,6-diamine and N-methyl-p-toluidine.

Example 39

1-{2-[(1R)-2,3-dihydro-1H-inden-1-ylamino]quinolin-6-yl}-3-[4-(pentafluoro-sulfanyl)phenyl]urea The title compound, MS: m/e=521.7 (M+H$^+$), was prepared in accordance with the general method 5 of example 34 from (R)—N$^2$-indan-1-yl-quinoline-2,6-diamine and 4-aminophenylsulphur pentafluoride.

Example 40

N-(4-chlorophenyl)-N'-{2-[(1R)-2,3-dihydro-1H-inden-1-ylamino]quinolin-6-yl}-N-methylsulfamide The title compound, MS: m/e=480.3 (M+H$^+$), was prepared in accordance with the general method 6 of example 37 from (R)—N$^2$-indan-1-yl-quinoline-2,6-diamine and 4-chloro-N-methylamine.

Example 41

N'-{2-[(1R)-2,3-dihydro-1H-inden-1-ylamino]quinolin-6-yl}-N-(4-fluorophenyl)-N-methylsulfamide The title compound, MS: m/e=463.9 (M+H$^+$), was prepared in accordance with the general method 6 of example 37 from (R)—N$^2$-indan-1-yl-quinoline-2,6-diamine and 4-fluoro-N-methylamin.

Example 42

1-(3,5-Dimethyl-isoxazol-4-yl)-3-[2-((R)-indan-1-ylamino)-quinolin-6-yl]-urea

The title compound, MS: m/e=414.6 (M+H$^+$), was prepared in accordance with the general method 4 of example 16 from (R)—N$^2$-indan-1-yl-quinoline-2,6-diamine and 3,5-dimethylisoxazol-4-yl isocyanate.

Example 43

N'-{2-[(1R)-2,3-dihydro-1H-inden-1-ylamino]quinolin-6-yl}-N-methyl-N-(4-methylbenzyl)sulfamide The title compound, MS: m/e=473.8 (M+H$^+$), was prepared in accordance with the general method 6 of example 37 from (R)—N²-indan-1-yl-quinoline-2,6-diamine and N-methyl-N-(4-methylbenzyl)amin.

Example 44

1-[2-((R)-Indan-1-ylamino)-quinolin-6-yl]-3-pyridin-2-yl-urea

The title compound, MS: m/e=396.7 (M+H⁺), was prepared in accordance with the general method 5 of example 34 from (R)—N²-indan-1-yl-quinoline-2,6-diamine and 2-aminopyridin.

Example 45

1-[2-((R)-Indan-1-ylamino)-quinolin-6-yl]-3-(3-methyl-3H-imidazol-4-ylmethyl)-urea The title compound, MS: m/e=413.7 (M+H⁺), was prepared in accordance with the general method 5 of example 34 from (R)—N²-indan-1-yl-quinoline-2,6-diamine and 1-methyl-5-aminomethylimidazole.

Example 46

N-(4-chlorobenzyl)-N'-{2-[(1R)-2,3-dihydro-1H-inden-1-ylamino]quinolin-6-yl}-N-methylsulfamide The title compound, MS: m/e=494.2 (M+H⁺), was prepared in accordance with the general method 6 of example 37 from (R)—N²-indan-1-yl-quinoline-2,6-diamine and N-methyl-N-(4-chlorobenzyl)amine.

Example 47

[2-((R)-Indan-1-ylamino)-quinolin-6-yl]-carbamic acid 4-methoxy-phenyl ester (R)—N²-Indan-1-yl-quinoline-2,6-diamine (0.070 g, 0.25 mmol) was dissolved in toluene (3 ml). 4-Methoxyphenyl chloroformate (0.042 mL, 0.28 mmol) and triethyl amine (0.053 mL, 0.38 mmol) were added and the reaction mixture was stirred at 60° C. for 10 h. Water (20 mL) was added and the mixture was extracted with ethyl acetate (3×15 mL). The combined organic phases were dried on sodium sulfate, filtered and the filtrate was evaporated. The crude product was purified by column chromatography (silica gel, heptane/ethyl acetate 4:1=>2:1) to yield the title compound as a colorless solid (33 mg, 31%); MS: m/e=326.6 (M+H⁺).

Example 48

N-(3-chlorophenyl)-N'-{2-[(1R)-2,3-dihydro-1H-inden-1-ylamino]quinolin-6-yl}-N-methylsulfamide The title compound, MS: m/e=480.2 (M+H⁺), was prepared in accordance with the general method 6 of example 37 from (R)—N²-indan-1-yl-quinoline-2,6-diamine and 3-chloro-N-methylanilin.

Example 49

N-[2-((R)-Indan-1-ylamino)-quinolin-6-yl]-2-thiophen-2-yl-acetamide (R)—N²-indan-1-yl-quinoline-2,6-diamine (0.10 g, 0.36 mmol), triethylamine (0.055 mL, 0.4 mmol) and 2-thiophen- acetyl chloride (0.049 mL, 0.4 mmol) were dissolved in toluene (3.0 mL). The reaction mixture was heated to 50° C. for 10 h. The reaction mixture was diluted with water and extracted with dichloromethane (3×). The combined organic phases were dried on sodium sulfate and evaporated. The crude product was purified by column chromatography (silica gel, heptane ethyl acetate 4:1/2:1/1:1/1:2). The title compound (0.077 g, 53%) was obtained as a yellow solid; MS: m/e=400.6 (M+H⁺).

Example 50

4-Fluoro-N-[2-((R)-indan-1-ylamino)-quinolin-6-yl]-benzamide

The title compound, MS: m/e=398.6 (M+H⁺), was prepared in accordance with the general method 8 of example 49 from (R)—N²-indan-1-yl-quinoline-2,6-diamine and 4-fluorobenzoyl chloride.

Example 51

2-(4-Fluoro-phenyl)-N-[2-((R)-indan-1-ylamino)-quinolin-6-yl]-acetamide (R)—N²-indan-1-yl-quinoline-2,6-diamine (0.05 g, 0.18 mmol), ethyldiisopropylamine (0.068 mL, 0.4 mmol), 1-(3-dimethylaminopropyl)-3-ethylcarbodiimide hydrochloride (EDC-HCl, 0.038 mg, 0.2 mmol), 2-(1H-benzotriazole-1-yl)-1,1,3,3-tetramethyluronium tetrafluoroborate (HOBt, 0.027 mg, 0.2 mmol) and 2-fluorophenyl acetic acid (0.031 mg, 0.2 mmol) were dissolved in tetrahydrofurane (3.0 mL). The reaction mixture was stirred at ambient temperature for 3 h. Then it was diluted with water and extracted with ethyl acetate (3×). The combined organic phases were dried on sodium sulfate and evaporated. The crude product was purified by column chromatography (silica gel, heptane, ethyl acetate 4:1/1:1). The title compound (0.025 g, 33%) was obtained as an off-white solid; MS: m/e=412.6 (M+H⁺).

Example 52

2-((R)-Indan-1-ylamino)-quinoline-6-carboxylic acid 4-fluoro-benzylamide

Step A: A stirred mixture of 2-chloro-quinoline-6-carboxylic acid ethyl ester [CAS-No. 29969-56-0] (500 mg, 2.12 mmol) and commercially available (R)-1-aminoindane (848 mg, 6.36 mmol) was heated in a sealed tube for 16 h at 120° C. Purification by flash chromatography on silica gel (ethyl acetate/heptane) yielded 2-((R)-indan-1-ylamino)-quinoline-6-carboxylic acid ethyl ester as a light brown solid (672 mg, 95%), MS (ISP) 333.2 [(M+H)⁺]; m.p. 137° C.

Step B: To a stirred solution of commercially available 4-fluoro-benzylamine (250 mg, 2.0 mmol) in dioxane (10 ml) was added drop wise at room temperature a 2M solution of trimethylaluminum in toluene (1 ml). The reaction mixture was allowed to stir for 1 h at room temperature, a solution of 2-((R)-indan-1-ylamino)-quinoline-6-carboxylic acid ethyl ester (166 mg, 0.5 mmol) in dioxane (4 ml) was added and the reaction mixture was heated for 2 h at 90° C. The reaction mixture was poured into 0.886M sodium-potassium-tartrate solution (25 ml) and extracted with ethyl acetate (2×40 ml). The combined organic layers were washed with brine (25 ml), dried (MgSO₄) and evaporated. The crude product was purified by flash chromatography (ethyl acetate/heptane) on silica gel and crystallization (dichloromethane/MeOH/hexane) to yield the title compound as an off-white solid (164 mg, 80%), MS (ISP) 412.2 [(M+H)+]; m.p. 175° C.

Example 53

(R)-Indan-1-yl-[6-(5-methyl-[1,2,4]oxadiazol-3-yl)-quinolin-2-yl]-amine

Step A: (R)-Indan-1-yl-(6-bromo-quinolin-2-yl)-amine, off-white solid, MS: m/e=339.0 (M+H+), was prepared in accordance with the general method of example 4, step A from commercially available 6-bromo-2-chloro-quinoline and commercially available (R)-indane-1-yl-amine.

Step B: A mixture of (R)-indan-1-yl-(6-bromo-quinolin-2-yl)-amine (1.14 g, 3.36 mmol), zinc cyanide (434 mg, 3.7 mmol) and tetrakis-(triphenylphosphine)-palladium (388 mg, 0.34 mmol) in DMF (12 ml) was heated at 160° C. for 15 min in a microwave reactor. The reaction mixture was poured into water (100 ml) and extracted with ethyl acetate (3×100 ml). The combined organic layers were washed with brine (2×50 ml), dried (MgSO$_4$) and evaporated. The crude product was purified by flash chromatography (ethyl acetate/heptane) on silica gel and crystallization (diethyl ether/heptane) to yield 2-((R)-indan-1-ylamino)-quinoline-6-carbonitrile as light yellow solid (310 mg, 32%).

M.p. 164.5° C.; MS: m/e=286.2 (M+H+).

Step C: A stirred suspension of 2-((R)-indan-1-ylamino)-quinoline-6-carbonitrile (143 mg, 0.5 mmol), hydroxylamine hydrochloride (129 mg, 1.86 mmol), sodium carbonate (106 mg, 1.0 mmol) in EtOH (2 ml) and water (2 ml) was heated under reflux conditions for 6 h, water (40 ml) was added, and the mixture was extracted with ethyl acetate (3×75 ml). The combined organic layers were washed with brine (20 ml), dried (MgSO$_4$) and evaporated to yield the crude product as solid which was further purified by crystallization (dichloromethane/methanol/heptane) to yield N-hydroxy-2-((R)-indan-1-ylamino)-quinoline-6-carboxamidine as off-white solid (140 mg, 88%).

MS: m/e=319.2 (M+H+); m.p. 236.5° C.

Step D: To a stirred solution of acetic acid (30 mg, 0.5 mmol) in acetonitrile (2.15 ml) was added at room temperature 1-hydroxy-benzotriazole (95 mg, 0.6 mmol) and N-(3-dimethylaminopropyl)-N'-ethyl-carbodiimid-hydrochloride (110 mg, 0.57 mmol). The mixture was allowed to stir for 3 h at room temperature and N-hydroxy-2-((R)-indan-1-ylamino)-quinoline-6-carboxamidine (107 mg, 0.34 mmol) was added together with acetonitrile (2.15 ml). The mixture was allowed to stir for 2 h at room temperature, evaporated to dryness and diluted with acetic acid (3.5 ml). The reaction mixture was allowed to stir for 2 h at 100° C., evaporated, poured into saturated NaHCO$_3$ solution (40 ml) and extracted with ethyl acetate (3×50 ml). The combined organic layers were washed with brine (2×50 ml), dried (MgSO$_4$) and evaporated. The crude product was purified by flash chromatography (ethyl acetate/heptane) on silica gel and crystallization (ethyl acetate/heptane) to yield the title compound as light yellow oil (110 mg, 64%).

MS: m/e=343.0 (M+H+)+).

Example 54

4-Fluoro-N-[2-((R)-indan-1-ylamino)-quinolin-6-ylmethyl]-benzamide

Step A: Hydrogenation of 2-((R)-indan-1-ylamino)-quinoline-6-carbonitrile (example 53, step B) (143 mg, 0.5 mmol) dissolved in methanol (7 ml) and 7N ammonia in methanol (3.5 ml) on Raney nickel (143 mg) for 16 h at room temperature yielded after removal of the catalyst by filtration and evaporation a yellow oil which was further purified by column chromatography (dichloromethane/methanol/ammonia 15:1:0.1) on silica gel to yield (6-aminomethyl-quinolin-2-yl)-(R)-indan-1-yl-amine as light yellow foam (130 mg, 90%).

MS: m/e=290.1 (M+H+).

Step B: To a cooled (ice bath) and stirred solution of (6-aminomethyl-quinolin-2-yl)-(R)-indan-1-yl-amine (130 mg, 0.45 mmol) and triethyl amine (50 mg, 0.49 mmol) in tetrahydrofurane (2.6 ml) was added 4-fluorobenzoyl chloride (78 mg, 0.49 mmol) and the mixture was allowed to stir at room temperature for 1 h. Evaporation and purification by flash chromatography (ethyl acetate/heptane) on silica gel yielded the title compound as white foam (150 mg, 81%). MS: m/e=412.2 (M+H+).

Example 55

2-((R)-Indan-1-ylamino)-quinoline-6-carboxylic acid 2-methoxy-benzylamide

The title compound, white solid, MS: m/e=424.2 (M+H+); m.p. 168° C., was prepared in accordance with the general method of example 52, step B, from 2-((R)-indan-1-ylamino)-quinoline-6-carboxylic acid ethyl ester (see example 52, step A) and commercially available 2-methoxy-benzylamine.

Example 56

(4-Fluoro-phenyl)-[2-((R)-indan-1-ylamino)-quinolin-6-yl]-methanone oxime

Step A: To a cooled (ice bath) and stirred suspension of 2-((R)-indan-1-ylamino)-quinoline-6-carbonitrile (example 53, step B) (230 mg, 0.81 mmol) in tetrahydrofurane (4 ml) was added drop wise a 1M solution of 4-fluorophenyl-magnesium bromide (2.4 ml, 2.43 mmol), the reaction mixture was heated under reflux conditions for 20 h and poured into ice-water (20 ml). 2N hydrochloride solution (5 ml) was added, the mixture was stirred at room temperature for 10 min, 3 N sodium hydroxide solution (5 ml) was added and the mixture was extracted with ethyl acetate (3×100 ml). The combined organic layers were washed with brine (2×50 ml), dried (MgSO$_4$) and evaporated. The crude product was purified by flash chromatography (ethyl acetate/heptane) on silica gel to yield (4-fluoro-phenyl)-[2-((R)-indan-1-ylamino)-quinolin-6-yl]-methanone as light yellow foam (220 mg, 71%). MS: m/e=383.2 (M+H+).

Step B: A stirred suspension of (4-fluoro-phenyl)-[2-((R)-indan-1-ylamino)-quinolin-6-yl]-methanone (100 mg, 0.26 mmol), hydroxylamine hydrochloride (55 mg, 0.79 mmol) and sodium carbonate (83 mg, 0.78 mmol) in ethanol (1 ml) was heated under reflux conditions for 17 h, the reaction mixture was poured into water (20 ml) and extracted with ethyl acetate (3×75 ml). The combined organic layers were washed with brine (50 ml), dried (MgSO$_4$) and evaporated. The crude product was further purified by flash chromatography on silica gel (heptane/ethyl acetate) and crystallization (ethyl acetate/heptane) to yield the title compound as white solid (61 mg, 59%).

MS: m/e=398.3 (M+H+); M.p. 225.5° C.

Example 57

2-((R)-Indan-1-ylamino)-quinoline-6-carboxylic acid (2,6-dimethoxy-phenyl)-amide The title compound, off-white solid, MS: m/e=444.4 (M+H$^+$); m.p. 199° C., was prepared in accordance with the general method of example 52, step B, from 2-((R)-indan-1-ylamino)-quinoline-6-carboxylic acid ethyl ester (see example 52, step A) and commercially available 2,6-dimethoxy-aniline.

Example 58

1-[2-((R)-Indan-1-ylamino)-quinolin-6-yl]-3-(2-methyl-2H-pyrazol-3-yl)-urea

The title compound, MS: m/e=499.6 (M+H$^+$), was prepared in accordance with the general method 5 of example 34 from (R)—N$^2$-indan-1-yl-quinoline-2,6-diamine and 5-amino-1-methylpyrazole.

Example 59

1-[2-((R)-Indan-1-ylamino)-quinolin-6-yl]-3-(2H-[1,2,4]triazol-3-yl)-urea

The title compound, MS: m/e=486.6 (M+H$^+$), was prepared in accordance with the general method 5 of example 34 from (R)—N$^2$-indan-1-yl-quinoline-2,6-diamine and 5H-[1,2,4]triazol-3-ylamine.

Example 60

1-[2-((R)-Indan-1-ylamino)-quinolin-6-yl]-3-thiazol-2-yl-urea

The title compound, MS: m/e=402.6 (M+H$^+$), was prepared in accordance with the general method 5 of example 34 from (R)—N$^2$-indan-1-yl-quinoline-2,6-diamine and 2-aminothiazole.

Example 61

(6-Imidazol-1-yl-quinolin-2-yl)-(R)-indan-1-yl-amine

A mixture of (6-bromo-quinolin-2-yl)-(R)-indan-1-yl-amine (see example 53, step A) (339 mg, 1.0 mmol), commercially available imidazole (136 mg, 2.0 mmol), copper(I) chloride (10 mg, 0.1 mmol), 2-acetyl-cyclohexanone (35 mg, 0.25 mmol), potassium carbonate (145 mg, 1.05 mmol) and 1-methyl-2-pyrrolidone (1 ml) was heated in a sealed tube at 130° C. for 18 h. The reaction mixture was poured into water (20 ml) and extracted with ethyl acetate (2×30 ml). The combined organic layers were washed with saturated sodium bicarbonate solution (2×20 ml) and brine (20 ml), dried (MgSO$_4$) and evaporated. Further purification of the crude product by flash chromatography on silica gel (ethyl acetate/heptane) yielded the title compound (186 mg, 57%) as off-white foam.
MS: m/e=327.3 (M+H$^+$).

Example 62

(R)-Indan-1-yl-(6-[1,2,4]triazol-1-yl-quinolin-2-yl)-amine

The title compound, pink gum, MS: m/e=328.3 (M+H$^+$), was prepared in accordance with the general method of example 61 from (6-bromo-quinolin-2-yl)-(R)-indan-1-yl-amine (see example 53, step A) and commercially available triazole.

Example 63

1-Benzoyl-3-[2-((R)-indan-1-ylamino)-quinolin-6-yl]-thiourea (R)-6-Amino-2-indanoyl-quinoline (1.2 g, 4.4 mmol) was dissolved in 50 mL acetone. Benzoyl-isothiocyanate (749 mg, 4.6 mmol) was added and the reaction mixture was stirred at room temperature overnight. The solvent was evaporated and the residue was purified by column chromatography (silica gel, dichloromethane/ethyl acetate 19:1). The title compound (1.55 g, 81%) was obtained as a light yellow foam; MS: m/e=439.1 (M+H$^+$).

Example 64

{6-[(4-Fluoro-benzylamino)-methyl]-quinolin-2-yl}-(R)-indan-1-yl-amine

A solution of (6-aminomethyl-quinolin-2-yl)-(R)-indan-1-yl-amine (example 54, step A) (130 mg, 0.45 mmol), 4-fluorobenzaldehyde (61 mg, 0.49 mmol) and acetic acid (108 mg, 1.8 mmol) in 1,2-dichloroethane (5 ml) was stirred at room temperature for 30 min. Afterwards sodium triacetoxy-borohydride (222 mg, 0.94 mmol) was added, the reaction mixture was allowed to stir for 2.5 days at room temperature, poured into ice/saturated sodium bicarbonate solution (30 ml) and extracted with dichloromethane (2×40 ml). The combined organic layers were washed with brine (30 ml), dried (MgSO$_4$) and evaporated. The crude product was purified by flash chromatography (ethyl acetate/heptane) on silica gel to yield the title compound as a colorless oil (99 mg, 55%). MS: m/e=398.3 (M+H$^+$).

Example 65

N-Benzyl-N'-[2-((R)-indan-1-ylamino)-quinolin-6-yl]-guanidine

Step A: 1-Benzoyl-3-[2-((R)-indan-1-ylamino)-quinolin-6-yl]-thiourea (1.5 g, 3.4 mmol) was suspended in 50 mL methanol. 4.1 mL 1N sodium hydroxide solution was added and the reaction mixture was refluxed for 2 h. The reaction mixture was diluted with 80 mL water and extracted with dichloromethane (2×100 mL). The organic phases were pooled, dried with sodium sulfate and evaporated. The residue was recrystallized from dichloromethane and diethylether. The title compound (660 mg, 58%) was obtained as an off-white solid; MS: m/e=335.3 (M+H$^+$).

Step B: [2-((R)-Indan-1-ylamino)-quinolin-6-yl]-thiourea (600 mg, 1.8 mmol) was dissolved in 20 mL acetone and 10 mL tetrahydrofurane. Methyliodide (306 mg, 2.2 mmol) was added and the reaction mixture was stirred at room temperature for 3 h. The solvent was evaporated and the residue was recrystallized from dichloromethane and diethylether. The title compound (720 mg, 84%) was obtained as a yellow solid; MS: m/e=349.4 (M+H$^+$).

Step C: 1-[2-((R)-Indan-1-ylamino)-quinolin-6-yl]-2-methyl-isothiourea hydroiodide (345 mg, 0.72 mmol) was dissolved in 10 mL ethanol. Benzylamine (310 mg, 2.9 mmol) was added and the reaction mixture was refluxed overnight. The solvent was evaporated and the residue was purified by column chromatography (silica gel, dichloromethane/metha-

Example 66

N²—(R)-Indan-1-yl-N6-pyrimidin-2-yl-quinoline-2, 6-diamine

Step A: A mixture of (6-bromo-quinolin-2-yl)-(R)-indan-1-yl-amine (see example 53, step A) (169.6 mg, 0.5 mmol), commercially available 2-amino-pyrimidine (95.1 mg, 1.0 mmol), XPhos (47.7 mg, 0.1 mmol), palladium(II)acetate (11.2 mg, 0.05 mmol), sodium tert.-butylate (96.1 mg, 1.0 mmol), tert-butanol (0.5 ml) and toluene (2.5 ml) was heated in a sealed tube at 130° C. for 16 h. The reaction mixture was poured into water (20 ml) and extracted with ethyl acetate (2×40 ml). The combined organic layers were washed with brine (20 ml), dried (MgSO$_4$) and evaporated. Further purification of the crude product by flash chromatography on silica gel (ethyl acetate/heptane) and crystallization (dichloromethane/methanol/hexane) yielded the title compound (64 mg, 36%) as off-white solid. MS: m/e=354.2 (M+H$^+$); m.p. 142° C.

Example 67

N$^6$-(4,6-Dimethyl-pyrimidin-2-yl)-N²—(R)-indan-1-yl-quinoline-2,6-diamine

The title compound, yellow solid, MS: m/e=382.3 (M+H$^+$); m.p. 88° C., was prepared in accordance with the general method of example 66 from (6-bromo-quinolin-2-yl)-(R)-indan-1-yl-amine (see example 53, step A) and commercially available 2-amino-4,6-dimethyl-pyrimidine.

Example 68

N²—(R)-Indan-1-yl-N$^6$-(4-methyl-pyrimidin-2-yl)-quinoline-2,6-diamine

The title compound, yellow solid, MS: m/e=368.2 (M+H$^+$); m.p. 103° C., was prepared in accordance with the general method of example 66 from (6-bromo-quinolin-2-yl)-(R)-indan-1-yl-amine (see example 53, step A) and commercially available 2-amino-4-methyl-pyrimidine.

Example 69

N²—(R)-Indan-1-yl-N$^6$-pyridin-2-yl-quinoline-2,6-diamine

The title compound, brown solid, MS: m/e=353.3 (M+H$^+$); m.p. 77° C., was prepared in accordance with the general method of example 66 from (6-bromo-quinolin-2-yl)-(R)-indan-1-yl-amine (see example 53, step A) and commercially available 2-amino-pyridine.

Example 70

N²—(R)-Indan-1-yl-N$^6$-(3-methyl-pyridin-2-yl)-quinoline-2,6-diamine

The title compound, light brown solid, MS: m/e=367.2 (M+H$^+$); m.p. 149° C., was prepared in accordance with the general method of example 66 from (6-bromo-quinolin-2-yl)-(R)-indan-1-yl-amine (see example 53, step A) and commercially available 2-amino-3-methyl-pyridine.

Example 71

N$^6$-(2-Ethyl-2H-tetrazol-5-yl)-N²—(R)-indan-1-yl-quinoline-2,6-diamine

The title compound, white solid, MS: m/e=372.3 (M+H$^+$); m.p. 159° C., was prepared in accordance with the general method of example 66 from (6-bromo-quinolin-2-yl)-(R)-indan-1-yl-amine (see example 53, step A) and commercially available 2-ethyl-2H-tetrazole-5-yl-amine.

Example 72

N²—(R)-Indan-1-yl-N$^6$-(6-methyl-pyridin-2-yl)-quinoline-2,6-diamine

The title compound, yellow foam, MS: m/e=367.2 (M+H$^+$); m.p. 72° C., was prepared in accordance with the general method of example 66 from (6-bromo-quinolin-2-yl)-(R)-indan-1-yl-amine (see example 53, step A) and commercially available 2-amino-6-methyl-pyridine.

Example 73

N²—(R)-Indan-1-yl-N$^6$-(4-trifluoromethyl-pyrimidin-2-yl)-quinoline-2,6-diamine The title compound, yellow solid, MS: m/e=422.2 (M+H$^+$); m.p. 165° C., was prepared in accordance with the general method of example 66 from (6-bromo-quinolin-2-yl)-(R)-indan-1-yl-amine (see example 53, step A) and commercially available 2-amino-4-trifluoromethyl-pyrimidine.

Example 74

N²—(R)-Indan-1-yl-N$^6$-(5-methyl-isoxazol-3-yl)-quinoline-2,6-diamine

The title compound, light brown solid, MS: m/e=357.3 (M+H$^+$)$^+$; m.p. 127° C., was prepared in accordance with the general method of example 66 from (6-bromo-quinolin-2-yl)-(R)-indan-1-yl-amine (see example 53, step A) and commercially available 5-methyl-isoxazole-3-yl-amine.

Example 75

N$^6$-(2-tert-Butyl-2H-tetrazol-5-yl)-N²—(R)-indan-1-yl-quinoline-2,6-diamine

The title compound, off-white solid, MS: m/e=400.3 (M+H$^+$); m.p. 146° C., was prepared in accordance with the general method of example 66 from (6-bromo-quinolin-2-yl)-(R)-indan-1-yl-amine (see example 53, step A) and commercially available 2-tert.-butyl-2H-tetrazole-5-yl-amine.

Example 76

N$^6$-(5-Cyclopropyl-[1,3,4]oxadiazol-2-yl)-N²—(R)-indan-1-yl-quinoline-2,6-diamine The title compound, off-white solid, MS: m/e=384.3 (M+H$^+$); m.p. 226° C., was prepared in accordance with the general method of example 66 from (6-bromo-quinolin-2- yl)-(R)-indan-1-yl-amine (see example 53, step A) and commercially available 5-cyclopropyl-1,3,4-oxadiazole-2-yl-amine.

Example 77

$N^2$—(R)-Indan-1-yl-$N^6$-(5-methyl-[1,3,4]oxadiazol-2-yl)-quinoline-2,6-diamine The title compound, white solid, MS: m/e=358.3 (M+H$^+$); m.p. 129° C., was prepared in accordance with the general method of example 66 from (6-bromo-quinolin-2-yl)-(R)-indan-1-yl-amine (see example 53, step A) and commercially available 5-methyl-1,3,4-oxadiazole-2-yl-amine.

Example 78

$N^2$—(R)-Indan-1-yl-$N^6$-(3-methyl-[1,2,4]oxadiazol-5-yl)-quinoline-2,6-diamine The title compound, light brown solid, MS: m/e=358.3 (M+H$^+$); m.p. 171° C., was prepared in accordance with the general method of example 66 from (6-bromo-quinolin-2-yl)-(R)-indan-1-yl-amine (see example 53, step A) and commercially available 3-methyl-1,2,4-oxadiazole-5-yl-amine [CAS-No. 3663-39-6].

Example 79

$N^2$—(R)-Indan-1-yl-$N^6$-(5-trifluoromethyl-[1,3,4]oxadiazol-2-yl)-quinoline-2,6-diamine The title compound, light brown solid, MS: m/e=412.2 (M+H$^+$); m.p. 146° C., was prepared in accordance with the general method of example 66 from (6-bromo-quinolin-2-yl)-(R)-indan-1-yl-amine (see example 53, step A) and commercially available 5-trifluoromethyl-1,3,4-oxadiazole-2-yl-amine.

Example 80

$N^2$—(R)-Indan-1-yl-$N^6$-(6-trifluoromethyl-pyridin-2-yl)-quinoline-2,6-diamine The title compound, light brown foam, MS: m/e=421.1 (M+H$^+$), was prepared in accordance with the general method of example 66 from (6-bromo-quinolin-2-yl)-(R)-indan-1-yl-amine (see example 53, step A) and commercially available 2-amino-6-trifluoromethyl-pyridine.

Example 81

$N^2$—(R)-Indan-1-yl-$N^6$-oxazol-2-yl-quinoline-2,6-diamine

The title compound, light yellow foam, MS: m/e=343.2 (M+H$^+$), was prepared in accordance with the general method of example 66 from (6-bromo-quinolin-2-yl)-(R)-indan-1-yl-amine (see example 53, step A) and commercially available oxazole-2-yl-amine [CAS-No. 4570-45-0].

Example 82

$N^2$—(R)-Indan-1-yl-$N^6$-(5-methyl-benzoxazol-2-yl)-quinoline-2,6-diamine

The title compound, light yellow solid, MS: m/e=407.3 (M+H$^+$); m.p. 171° C., was prepared in accordance with the general method of example 66 from (6-bromo-quinolin-2-yl)-(R)-indan-1-yl-amine (see example 53, step A) and commercially available 5-methyl-benzoxazol-2-yl-amine [CAS-No. 64037-15-6].

Example 83

2-{3-[2-((R)-Indan-1-ylamino)-quinolin-6-ylamino]-phenyl}-ethanol

The title compound, yellow solid, MS: m/e=396.4 (M+H$^+$); m.p. 109° C., was prepared in accordance with the general method of example 66 from (6-bromo-quinolin-2-yl)-(R)-indan-1-yl-amine (see example 53, step A) and commercially available 3-(2-hydroxyethyl)-aniline.

Example 84

$N^2$—(R)-Indan-1-yl-$N^6$-(3-piperidin-1-yl-[1,2,4]oxadiazol-5-yl)-quinoline-2,6-diamine The title compound, white solid, MS: m/e=427.3 (M+H$^+$); m.p. 157° C., was prepared in accordance with the general method of example 66 from (6-bromo-quinolin-2-yl)-(R)-indan-1-yl-amine (see example 53, step A) and 3-(piperidin-1-yl)-[1,2,4]oxadiazol-5-yl-amine [CAS-No. 75565-19-4].

Example 85

$N^2$—(R)-Indan-1-yl-$N^6$-methyl-$N^6$-pyridin-2-yl-quinoline-2,6-diamine

The title compound, light yellow foam, MS: m/e=367.2 (M+H$^+$), was prepared in accordance with the general method of example 66 from (6-bromo-quinolin-2-yl)-(R)-indan-1-yl-amine (see example 53, step A) and commercially available 2-(methylamino)-pyridine.

Example 86

$N^2$—(R)-Indan-1-yl-$N^6$-(5-methoxymethyl-[1,3,4]oxadiazol-2-yl)-quinoline-2,6-diamine The title compound, off-white solid, MS: m/e=388.3 (M+H$^+$); m. p. 169.5° C., was prepared in accordance with the general method of example 66 from (6-bromo-quinolin-2-yl)-(R)-indan-1-yl-amine (see example 53, step A) and commercially available 5-methoxymethyl-[1,3,4]oxadiazol-5-yl-amine [CAS. No. 302842-60-0].

Example 87

$N^2$—(R)-Indan-1-yl-$N^6$-(3-morpholin-4-yl-[1,2,4]oxadiazol-5-yl)-quinoline-2,6-diamine The title compound, off-white solid, MS: m/e=429.3 (M+H$^+$); m. p. 166° C., was prepared in accordance with the general method of example 66 from (6-bromo-quinolin-2-yl)-(R)-indan-1-yl-amine (see example 53, step A) and 3-morpholin-4-yl-[1,2,4]oxadiazol-5-yl-amine (prepared according to J. W. Tilley, H. Ramuz, Helvetica Chimica Acta 63(4), 1980, 832-840; white solid, m.p. 187° C.).

Example 88

$N^2$—(R)-Indan-1-yl-$N^6$-(3-phenyl-[1,2,4]oxadiazol-5-yl)-quinoline-2,6-diamine The title compound, light yellow solid, MS: m/e=420.2 (M+H$^+$); m. p. 203° C., was prepared in accordance with the general method of example 66 from (6-bromo-quinolin-2-yl)-(R)-indan-1-yl-amine (see example 53, step A) and commercially available 3-phenyl-[1,2,4]oxadiazol-5-yl-amine [CAS. No. 3663-37-4].

Example 89

N²—(R)-Indan-1-yl-N⁶-[3-(4-methyl-piperazin-1-yl)-[1,2,4]oxadiazol-5-yl]-quinoline-2,6-diamine The title compound, light yellow solid, MS: m/e=442.3 (M+H⁺); m. p. 190° C., was prepared in accordance with the general method of example 66 from (6-bromo-quinolin-2-yl)-(R)-indan-1-yl-amine (see example 53, step A) and 3-(4-methyl-piperazin-1-yl)-[1,2,4]oxadiazol-5-yl-amine [CAS. No. 343792-01-8].

Example 90 rac-N-[2-(5-Fluoro-indan-1-ylamino)-quinolin-6-yl]-2-pyridin-4-yl-acetamide

The title compound, off-white solid, MS: m/e=413.2 (M+H⁺), was prepared in accordance with the general method of example 6 from rac-N²-(5-fluoro-indan-1-yl)-quinoline-2,6-diamine (see example 6, step A+B) and 4-pyridyl-acetic acid.

Example 91 rac-N²-(7-Methoxy-indan-1-yl)-N⁶-(6-trifluoromethyl-pyridin-2-yl)-quinoline-2,6-diamine Step A: Rac-(6-Bromo-quinolin-2-yl)-(7-methoxy-indan-1-yl)-amine, yellow solid, MS: m/e=371.0 (M+H⁺); m. p. 129° C., was prepared in accordance with the general method of example 4, step A from commercially available 6-bromo-2-chloro-quinoline and 7-methoxy-indane-1-yl-amine [CAS. No. 215362-49-5 and 215362-48-4].
Step B: The title compound, off-white solid, MS: m/e=451.0 (M+H+); m. p. 126° C., was prepared in accordance with the general method of example 66 from rac-(6-bromo-quinolin-2-yl)-(7-methoxy-indan-1-yl)-amine (see example 91, step A) and commercially available 2-amino-6-trifluoromethyl-pyridine.

Example 92 rac-N²-(7-Methoxy-indan-1-yl)-N⁶-(4-trifluoromethyl-pyrimidin-2-yl)-quinoline-2,6-diamine The title compound, yellow solid, MS: m/e=452.0 (M+H⁺); m. p. 196° C., was prepared in accordance with the general method of example 66 from rac-(6-bromo-quinolin-2-yl)-(7-methoxy-indan-1-yl)-amine (see example 91, step A) and commercially available 2-amino-4-trifluoromethyl-pyrimidine.

Example 93 rac-N⁶-(4,6-Dimethyl-pyrimidin-2-yl)-N²-(7-methoxy-indan-1-yl)-quinoline-2,6-diamine The title compound, light brown solid, MS: m/e=412.3 (M+H+); m. p. 150° C., was prepared in accordance with the general method of example 66 from rac-(6-bromo-quinolin-2-yl)-(7-methoxy-indan-1-yl)-amine (see example 91, step A) and commercially available 2-amino-4,6-dimethyl-pyrimidine.

Example 94 rac-N²-(7-Methoxy-indan-1-yl)-N⁶-(6-methyl-pyridin-2-yl)-quinoline-2,6-diamine

The title compound, yellow foam, MS: m/e=397.3 (M+H+), was prepared in accordance with the general method of example 66 from rac-(6-bromo-quinolin-2-yl)-(7-methoxy-indan-1-yl)-amine (see example 91, step A) and commercially available 2-amino-6-methyl-pyridine.

Example 95 rac-N²-(7-Methoxy-indan-1-yl)-N⁶-(5-methyl-isoxazol-3-yl)-quinoline-2,6-diamine

The title compound, off-white solid, MS: m/e=387.3 (M+H+); m. p. 109° C., was prepared in accordance with the general method of example 66 from rac-(6-bromo-quinolin-2-yl)-(7-methoxy-indan-1-yl)-amine (see example 91, step A) and commercially available 5-methyl-isoxazole-3-yl-amine.

Example 96 rac-N²-(2,3-Dihydro-benzofuran-3-yl)-N⁶-(6-trifluoromethyl-pyridin-2-yl)-quinoline-2,6-diamine Step A: Rac-(6-Bromo-quinolin-2-yl)-(2,3-dihydro-benzofuran-3-yl)-amine, light yellow solid, MS: m/e=343.1 (M+H+); m. p. 101.5° C., was prepared in accordance with the general method of example 4, step A from commercially available 6-bromo-2-chloro-quinoline and commercially available 2,3-dihydro-benzofuran-3-yl-amine [CAS. No. 109926-35-4].
Step B: The title compound, light yellow foam, MS: m/e=423.2 (M+H+), was prepared in accordance with the general method of example 66 from rac-(6-bromo-quinolin-2-yl)-(2,3-dihydro-benzofuran-3-yl)-amine (see example 96, step A) and commercially available 2-amino-6-trifluoromethyl-pyridine.

Example 97 rac-N²-(2,3-Dihydro-benzofuran-3-yl)-N⁶-(4,6-dimethyl-pyrimidin-2-yl)-quinoline-2,6-diamine The title compound, light yellow solid, MS: m/e=384.2 (M+H+); m. p. 213° C., was prepared in accordance with the general method of example 66 from rac-(6-bromo-quinolin-2-yl)-(2,3-dihydro-benzofuran-3-yl)-amine (see example 96, step A) and commercially available 2-amino-4,6-dimethyl-pyrimidine.

Example 98 rac-N²-(2,3-Dihydro-benzofuran-3-yl)-N⁶-(4-trifluoromethyl-pyrimidin-2-yl)-quinoline-2,6-diamine The title compound, white solid, MS: m/e=424.2 (M+H+); m. p. 128° C., was prepared in accordance with the general method of example 66 from rac-(6-bromo-quinolin-2-yl)-(2, 3-dihydro-benzofuran-3-yl)-amine (see example 96, step A) and commercially available 2-amino-4-trifluoromethyl-pyrimidine.

Example 99 rac-N²-(2,3-Dihydro-benzofuran-3-yl)-N⁶-(6-methyl-pyridin-2-yl)-quinoline-2,6-diamine The title compound, light yellow foam, MS: m/e=369.2 (M+H+), was prepared in accordance with the general method of example 66 from rac-(6-bromo-quinolin-2-yl)-(2,3-dihydro-benzofuran-3-yl)-amine (see example 96, step A) and commercially available 2-amino-6-methyl-pyridine.

Example 100 rac-2-Imidazol-1-yl-N-[2-(7-methoxy-indan-1-ylamino)-quinolin-6-yl]-acetamide

The title compound was prepared in accordance with the general method described in example 6 from rac-N²-(7-methoxy-indan-1-yl)-quinoline-2,6-diamine and imidazol-1-yl-acetic acid; MS: m/e=414.3 (M+H⁺).

Example 101 rac-N²-(2,3-Dihydro-benzofuran-3-yl)-N⁶-(5-methyl-isoxazol-3-yl)-quinoline-2,6-diamine The title compound, off-white solid, MS: m/e=359.2 (M+H⁺); m. p. 195° C., was prepared in accordance with the general method of example 66 from rac-(6-bromo-quinolin-2-yl)-(2,3-dihydro-benzofuran-3-yl)-amine (see example 96, step A) and commercially available 5-methyl-isoxazole-3-yl-amine.

Example 102 rac-N²-(5-Fluoro-indan-1-yl)-N⁶-(6-trifluoromethyl-pyridin-2-yl)-quinoline-2,6-diamine Step A: Rac-(6-Bromo-quinolin-2-yl)-(5-fluoro-indan-1-yl)-amine, light brown oil, MS: m/e=259.1 (M+H⁺), was prepared in accordance with the general method of example 4, step A from commercially available 6-bromo-2-chloro-quinoline and commercially available 5-fluoro-indane-1-yl-amine [CAS. No. 148960-33-2].

Step B: The title compound, yellow foam, MS: m/e=439.2 (M+H⁺), was prepared in accordance with the general method of example 66 from rac-(6-bromo-quinolin-2-yl)-(5-fluoro-indan-1-yl)-amine (see example 102, step A) and commercially available 2-amino-6-trifluoromethyl-pyridine.

Example 103 rac-N²-(5-Fluoro-indan-1-yl)-N⁶-(4-trifluoromethyl-pyrimidin-2-yl)-quinoline-2,6-diamine The title compound, light yellow solid, MS: m/e=440.2 (M+H⁺); m. p. 112° C., was prepared in accordance with the general method of example 66 from rac-(6-bromo-quinolin-2-yl)-(5-fluoro-indan-1-yl)-amine (see example 102, step A) and commercially available 2-amino-4-trifluoromethyl-pyrimidine.

Example 104 rac-N⁶-(4,6-Dimethyl-pyrimidin-2-yl)-N²-(7-methoxy-indan-1-yl)-quinoline-2,6-diamine The title compound, light yellow foam, MS: m/e=400.3 (M+H⁺), was prepared in accordance with the general method of example 66 from rac-(6-bromo-quinolin-2-yl)-(5-fluoro-indan-1-yl)-amine (see example 102, step A) and commercially available 2-amino-4,6-dimethyl-pyrimidine.

Example 105 rac-N²-(5-Fluoro-indan-1-yl)-N⁶-(6-methyl-pyridin-2-yl)-quinoline-2,6-diamine

The title compound, yellow foam, MS: m/e=385.3 (M+H⁺), was prepared in accordance with the general method of example 66 from rac-(6-bromo-quinolin-2-yl)-(5-fluoro-indan-1-yl)-amine (see example 102, step A) and commercially available 2-amino-6-methyl-pyridine.

Example 106 rac-N²-(5-Fluoro-indan-1-yl)-N⁶-(5-methyl-isoxazol-3-yl)-quinoline-2,6-diamine

The title compound, off-white solid, MS: m/e=375.3 (M+H⁺); m. p. 166° C., was prepared in accordance with the general method of example 66 from rac-(6-bromo-quinolin-2-yl)-(7-methoxy-indan-1-yl)-amine (see example 102, step A) and commercially available 5-methyl-isoxazole-3-yl-amine.

Example 107 rac-N-[2-(7-Fluoro-indan-1-ylamino)-quinolin-6-yl]-2-[1,2,4]triazol-1-yl-acetamide The title compound was prepared in accordance with the general method described in example 6 from rac-N²-(7-fluoro-indan-1-yl)-quinoline-2,6-diamine and 1,2,4-triazol-1-acetic acid; MS: m/e=401.5 (M−H⁺).

Example 108 rac-N-[2-(7-Fluoro-indan-1-ylamino)-quinolin-6-yl]-2-thiazol-4-yl-acetamide

The title compound was prepared in accordance with the general method described in example 6 from rac-N²-(7-fluoro-indan-1-yl)-quinoline-2,6-diamine and 4-thiazole acetic acid (CAS 7504-44-1); MS: m/e=419.1 (M+H⁺).

Example 109 rac-N²-(4-Methoxy-2,3-dihydro-benzofuran-3-yl)-N⁶-(6-trifluoromethyl-pyridin-2-yl)-quinoline-2,6-diamine Step A: A mixture of 4-methoxy-benzofuran-3-one (CAS 7169-35-9) (4.9 g, 19 mmol), sodium acetate (3.06 g, 38 mmol) and hydroxylamine hydrochloride (2.58 g, 38 mmol) in ethanol (40 ml) was refluxed for 6 h. Cooled to room temperature, filtered the precipitate off, washed with ethanol and dried in high vacuum to give 4-methoxy-benzofuran-3-one oxime as a white solid (5.93 g, 100%); MS: m/e=180.2 (M+H+).

Step B: A mixture of the above described 4-methoxy-benzofuran-3-one oxime (6.15 g, 34.3 mmol) in ethanol (500 ml) with 10% palladium on charcoal (6.15 g) was hydrogenated at 23° C. and atmospheric pressure for 18 h. Filtered the catalyst off, washed with ethanol, evaporated the filtrate totally and dried in high vacuum to give rac-4-methoxy-2,3-dihydro-benzofuran-3-ylamine as a light yellow oil (3.65 g, 64%); MS: m/e=166.2 (M+H+).

Step C: Rac-(6-Bromo-quinolin-2-yl)-(4-methoxy-2,3-dihydro-benzofuran-3-yl)-amine, yellow solid, MS: m/e=373.1 (M+H+); m. p. 143° C., was prepared in accordance with the general method of example 4, step A from commercially available 6-bromo-2-chloro-quinoline and rac-4-methoxy-2,3-dihydro-benzofuran-3-ylamine.

Step D: The title compound, light yellow solid, MS: m/e=453.1 (M+H+); m. p. 132° C., was prepared in accordance with the general method of example 66 from rac-(6-bromo-quinolin-2-yl)-(4-methoxy-2,3-dihydro-benzofuran-3-yl)-amine (see example 109, step C) and commercially available 2-amino-6-trifluoromethyl-pyridine.

Example 110 rac-N$^2$-(4-Methoxy-2,3-dihydro-benzofuran-3-yl)-N$^6$-(4-trifluoromethyl-pyrimidin-2-yl)-quinoline-2,6-diamine The title compound, light yellow solid, MS: m/e=454.1 (M+H+); m. p. 185° C., was prepared in accordance with the general method of example 66 from rac-(6-bromo-quinolin-2-yl)-(4-methoxy-2,3-dihydro-benzofuran-3-yl)-amine (see example 109, step C) and commercially available 2-amino-4-trifluoromethyl-pyrimidine.

Example 111 rac-N$^6$-(4,6-Dimethyl-pyrimidin-2-yl)-N$^2$-(4-methoxy-2,3-dihydro-benzofuran-3-yl)-quinoline-2,6-diamine The title compound, light yellow solid, MS: m/e=414.4 (M+H+); m. p. 145° C., was prepared in accordance with the general method of example 66 from rac-(6-bromo-quinolin-2-yl)-(4-methoxy-2,3-dihydro-benzofuran-3-yl)-amine (see example 109, step C) and commercially available 2-amino-4,6-dimethyl-pyrimidine.

Example 112 rac-N$^2$-(4-Methoxy-2,3-dihydro-benzofuran-3-yl)-N$^6$-(6-methyl-pyridin-2-yl)-quinoline-2,6-diamine The title compound, yellow foam, MS: m/e=399.2 (M+H+), was prepared in accordance with the general method of example 66 from rac-(6-bromo-quinolin-2-yl)-(4-methoxy-2,3-dihydro-benzofuran-3-yl)-amine (see example 109, step C) and commercially available 2-amino-6-methyl-pyridine.

Example 113 rac-N$^2$-(4-Methoxy-2,3-dihydro-benzofuran-3-yl)-N$^6$-(5-methyl-isoxazol-3-yl)-quinoline-2,6-diamine The title compound, off-white solid, MS: m/e=389.3 (M+H+); m. p. 222° C., was prepared in accordance with the general method of example 66 from rac-(6-bromo-quinolin-2-yl)-(4-methoxy-2,3-dihydro-benzofuran-3-yl)-amine (see example 109, step C) and commercially available 5-methyl-isoxazol-3-yl-amine.

Example 114 rac-N-[2-(7-Methoxy-indan-1-ylamino)-quinolin-6-yl]-2-[1,2,4]triazol-4-yl-acetamide The title compound was prepared in accordance with the general method described in example 6 from rac-N$^2$-(7-methoxy-indan-1-yl)-quinoline-2,6-diamine and 2-(1,2,4-triazol-1-acetic acid; MS: m/e=413.5 (M–H+).

Example 115 rac-N-[2-(7-Methoxy-indan-1-ylamino)-quinolin-6-yl]-2-pyridin-4-yl-acetamide

The title compound was prepared in accordance with the general method described in example 6 from rac-N$^2$-(7-methoxy-indan-1-yl)-quinoline-2,6-diamine and 4-pyridine-acetic acid; MS: m/e=425.3 (M+H+).

The invention claimed is:

1. A compound of formula (I)

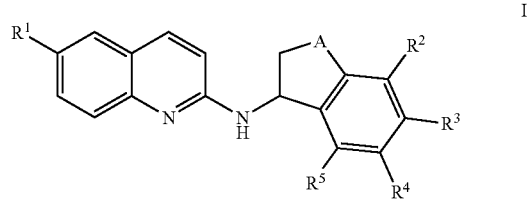

wherein
A is —CH$_2$— or —O—,
R$^1$ is 5-membered heteroaryl, —C(=NR$^a$)—Ar$^1$, —NR$^b$—Ar$^1$, —C(O)—NH—Ar$^1$, —NH—C(O)—Ar$^1$, —NH—S(O)$_2$—Ar$^1$, —NH—CH$_2$—Ar$^1$, —O—CH$_2$—Ar$^1$, —CH$_2$—NH—C(O)—Ar$^1$, —C(O)—NH—CH$_2$—Ar$^1$, —CH$_2$—NH—CH$_2$—Ar$^1$, —NH—S(O)$_2$—NR$^c$—Ar$^1$, —NR$^d$—C(O)—NR$^e$—Ar$^1$, —NH—C(O)—CH$_2$—Ar$^1$, —NH—C(O)—O—Ar$^1$, —NH—C(O)—NH—CHR$^f$—Ar$^1$, —NH—C(=NR$^a$)—NH—CH$_2$—Ar$^1$, —NH—(CH$_2$)$_3$—Ar$^1$, or —NH—C(S)—NH—C(O)—Ar$^1$,
R$^a$ is H, OH, or alkyl,
R$^b$, R$^c$, R$^d$, R$^e$, and R$^f$ are each independently H, alkyl, or allyl,
Ar$^1$ is phenyl or 5- to 10-membered monocyclic or bicyclic heteroaryl,
each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy, R$^2$, R$^3$, R$^4$ and R$^5$ are independently selected from H, halo, alkyl and alkoxy;
or a pharmaceutically acceptable salt thereof.
2. The compound of claim 1, wherein A is —CH$_2$—.
3. The compound of claim 1, wherein A is —O—.

4. The compound of claim 1, wherein
R¹ is imidazolyl,
  [1,2,4]-oxadiazolyl,
  [1,2,4]-triazolyl,
  —C(=NR$^a$)—Ar¹, wherein R$^a$ is OH, H or alkyl;
  —NR$^e$—Ar¹, wherein R$^a$ is H or alkyl,
  —C(O)—NH—Ar¹,
  —NH—C(O)—Ar¹,
  —NH—S(O)$_2$—Ar¹,
  —NH—CH$_2$—Ar¹,
  —O—CH$_2$—Ar¹,
  —CH$_2$—NH—C(O)—Ar¹,
  —C(O)—NH—CH$_2$—Ar¹,
  —CH$_2$—NH—CH$_2$—Ar¹,
  —NH—S(O)$_2$—NR$^c$—Ar¹, wherein R$^c$ is H or alkyl,
  —NR$^d$—C(O)—NR$^e$—Ar¹, wherein R$^d$ and R$^f$ are each independently H, alkyl, or allyl;
  —NH—C(O)—CH$_2$—Ar¹,
  —NH—C(O)—O—Ar¹,
  —NH—C(O)—NH—CHR$^f$—Ar¹, wherein R$^f$ is independently H or alkyl,
  —NH—C(=NR$^a$)—NH—CH$_2$—Ar¹, wherein R$^a$ is OH, H or alkyl;
  —NH—(CH$_2$)$_3$—Ar¹, or
  —NH—C(S)—NH—C(O)—Ar¹.

5. The compound of claim 1, wherein
R¹ is —NR$^b$—Ar¹, wherein R$^b$ is H or alkyl,
  —NH—C(O)—Ar¹,
  —NH—S(O)$_2$—Ar¹,
  —NH—CH$_2$—Ar¹,
  —O—CH$_2$—Ar¹,
  —NH—S(O)$_2$—NR$^c$—Ar¹, wherein R$^c$ is H or alkyl,
  —NR$^d$—C(O)—NR$^e$—Ar¹, wherein R$^d$ and R$^f$ are each independently H, alkyl, or allyl;
  —NH—C(O)—CH$_2$—Ar¹,
  —NH—C(O)—O—Ar¹, or
  —NH—C(O)—NH—CHR$^f$—Ar¹, wherein R$^f$ is independently H or alkyl.

6. The compound of claim 1, wherein Ar¹ is phenyl or 5- to 10-membered monocyclic or bicyclic heteroaryl, each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

7. The compound of claim 1, wherein Ar¹ is phenyl or 5- to 10-membered monocyclic or bicyclic heteroaryl, each of which is unsubstituted or substituted by one or more halo, alkyl, haloalkyl, hydroxyalkyl, cycloalkyl, -alkylene-O-alkyl, alkoxy, —S(O)$_2$-alkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

8. The compound of claim 1, wherein Ar¹ is phenyl, thiophenyl, furanyl, pyrrolyl, imidazolyl, pyrazolyl, oxazolyl, isoxazolyl, thiazolyl, isothiazolyl, [1,2,4]oxadiazolyl, [1,3,4]oxadiazolyl, [1,2,4]triazolyl, [1,2,3]triazolyl, tetrazolyl, pyridinyl, pyrimidinyl, pyrazinyl, pyridazinyl, indolyl, or benzoxazolyl, each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

9. The compound of claim 1, wherein Ar¹ is phenyl, thiophenyl, imidazolyl, pyrazolyl, oxazolyl, isoxazolyl, thiazolyl, [1,2,4]oxadiazolyl, [1,3,4]oxadiazolyl, [1,2,4]triazolyl, tetrazolyl, pyridinyl, pyrimidinyl, indolyl, or benzoxazolyl, each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

10. The compound of claim 1, wherein Ar¹ is phenyl, thiophenyl, imidazolyl, pyrazolyl, oxazolyl, isoxazolyl, thiazolyl, [1,2,4]oxadiazolyl, [1,3,4]oxadiazolyl, [1,2,4]triazolyl, tetrazolyl, pyridinyl, pyrimidinyl, indolyl, or benzoxazolyl, each of which is unsubstituted or substituted by one or more halo, alkyl, haloalkyl, hydroxyalkyl, cycloalkyl, -alkylene-O-alkyl, alkoxy, —S(O)$_2$-alkyl, —SF$_5$, or 5- to 6-membered heterocycloalkyl.

11. The compound of claim 1, wherein Ar¹ is phenyl, [1,2,4]oxadiazol-3-yl, [1,2,4]oxadiazol-5-yl, [1,2,4]triazol-1-yl, [1,2,4]triazol-3-yl, [1,2,4]triazol-4-yl, [1,3,4]oxadiazol-2-yl, 1H-indol-4-yl, benzoxazol-2-yl, imidazol-1-yl, imidazol-2-yl, imidazol-4-yl, isoxazol-3-yl, oxazol-2-yl, pyrazol-3-yl, pyridin-2-yl, pyridin-3-yl, pyridin-4-yl, pyrimidin-2-yl, tetrazol-5-yl, thiazol-2-yl, thiazol-2-yl, thiazol-4-yl, or thiophen-2-yl, each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

12. The compound of claim 1, wherein Ar¹ is phenyl, [1,2,4]oxadiazol-3-yl, [1,2,4]oxadiazol-5-yl, [1,2,4]triazol-1-yl, [1,2,4]triazol-3-yl, [1,2,4]triazol-4-yl, [1,3,4]oxadiazol-2-yl, 1H-indol-4-yl, benzoxazol-2-yl, imidazol-1-yl, imidazol-2-yl, imidazol-4-yl, isoxazol-3-yl, oxazol-2-yl, pyrazol-3-yl, pyridin-2-yl, pyridin-3-yl, pyridin-4-yl, pyrimidin-2-yl, tetrazol-5-yl, thiazol-2-yl, thiazol-2-yl, thiazol-4-yl, or thiophen-2-yl, each of which is unsubstituted or substituted by one or more halo, alkyl, haloalkyl, hydroxyalkyl, cycloalkyl, -alkylene-O-alkyl, alkoxy, —S(O)$_2$-alkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy.

13. The compound of claim 1, wherein R² and R⁴ are H.

14. The compound of claim 1, wherein R³ is H or halo.

15. The compound of claim 14, wherein R³ is H or fluoro.

16. The compound of claim 1, wherein R⁵ is H, halo or alkoxy.

17. The compound of claim 16, wherein R⁵ is H, fluoro or methoxy.

18. The compound of claim 1, wherein R² and R⁴ are H, R³ is H or halo, and R⁵ is H, halo, or alkoxy.

19. The compound of claim 1, selected from the group consisting of
  [6-(4-Fluoro-benzyloxy)-quinolin-2-yl]-(R)-indan-1-yl-amine;

(R)-Indan-1-yl-[6-(3-methoxy-benzyloxy)-quinolin-2-yl]-amine;
(R)-Indan-1-yl-[6-(pyridin-3-ylmethoxy)-quinolin-2-yl]-amine;
$N^2$—(R)-Indan-1-yl-$N^6$-pyridin-3-ylmethyl-quinoline-2,6-diamine;
$N^2$—(R)-Indan-1-yl-$N^6$-(1-methyl-1H-imidazol-2-ylmethyl)-quinoline-2,6-diamine;
rac-N-[2-(5-Fluoro-indan-1-ylamino)-quinolin-6-yl]-2-pyridin-3-yl-acetamide;
$N^2$—(R)-Indan-1-yl-$N^6$-(3-methyl-3H-imidazol-4-ylmethyl)-quinoline-2,6-diamine;
$N^2$—(R)-Indan-1-yl-$N^6$-(3-methanesulfonyl-benzyl)-quinoline-2,6-diamine;
$N^6$-(3-Imidazol-1-yl-propyl)-$N^2$—(R)-indan-1-yl-quinoline-2,6-diamine;
$N^2$—(R)-Indan-1-yl-$N^6$-(1-methyl-1H-imidazol-4-ylmethyl)-quinoline-2,6-diamine; and
$N^2$—(R)-Indan-1-yl-$N^6$-(1-H-indol-4-ylmethyl)-quinoline-2,6-diamine.

20. The compound of claim 1, selected from the group consisting of
$N^6$-(1H-Imidazol-2-ylmethyl)-$N^2$—(R)-indan-1-yl-quinoline-2,6-diamine;
$N^2$—(R)-Indan-1-yl-$N^6$-thiazol-2-ylmethyl-quinoline-2,6-diamine;
4-Fluoro-N-[2-((R)-indan-1-ylamino)-quinolin-6-yl]-benzenesulfonamide;
$N^2$—(R)-Indan-1-yl-$N^6$-pyridin-4-ylmethyl-quinoline-2,6-diamine;
1-[2-((R)-Indan-1-ylamino)-quinolin-6-yl]-3-phenyl-urea;
$N^2$—(R)-Indan-1-yl-$N^6$-(5-methyl-3-H-imidazol-4-ylmethyl)-quinoline-2,6-diamine;
$N^2$—(R)-Indan-1-yl-$N^6$-(1-H-pyrazol-3-ylmethyl)-quinoline-2,6-diamine;
1-(4-Fluoro-phenyl)-3-[2-((R)-indan-1-ylamino)-quinolin-6-yl]-urea;
1-(3-Fluoro-phenyl)-3-[2-((R)-indan-1-ylamino)-quinolin-6-yl]-urea;
1-[2-((R)-Indan-1-ylamino)-quinolin-6-yl]-3-(4-methoxy-phenyl)-urea; and
1-[2-((R)-Indan-1-ylamino)-quinolin-6-yl]-3-(3-methoxy-phenyl)-urea.

21. The compound of claim 1, selected from the group consisting of
1-[2-((R)-Indan-1-ylamino)-quinolin-6-yl]-3-(2-methoxy-phenyl)-urea;
1-Allyl-1-[2-((R)-indan-1-ylamino)-quinolin-6-yl]-3-(4-methoxy-phenyl)-urea;
1-(2-Fluoro-phenyl)-3-[2-((R)-indan-1-ylamino)-quinolin-6-yl]-urea;
3-[2-((R)-Indan-1-ylamino)-quinolin-6-yl]-1-methyl-1-phenyl-urea;
1-[2-((R)-Indan-1-ylamino)-quinolin-6-yl]-3-((R)-1-phenyl-ethyl)-urea;
1-[2-((R)-Indan-1-ylamino)-quinolin-6-yl]-3-((S)-1-phenyl-ethyl)-urea;
1-[2-((R)-Indan-1-ylamino)-quinolin-6-yl]-3-(4-methoxy-benzyl)-urea;
1-[2-((R)-Indan-1-ylamino)-quinolin-6-yl]-3-(4-trifluoromethyl-phenyl)-urea;
1-(6-Chloro-pyridin-3-yl)-3-[2-((R)-indan-1-ylamino)-quinolin-6-yl]-urea;
1-[2-((R)-Indan-1-ylamino)-quinolin-6-yl]-3-(4-methoxy-phenyl)-1-propyl-urea; and
1-(2-Chloro-pyridin-4-yl)-3-[2-((R)-indan-1-ylamino)-quinolin-6-yl]-urea.

22. The compound of claim 1, selected from the group consisting of
1-(2-Bromo-6-methyl-pyridin-4-yl)-3-[2-((R)-indan-1-ylamino)-quinolin-6-yl]-urea;
1-(2-Bromo-3-methyl-pyridin-4-yl)-3-[2-((R)-indan-1-ylamino)-quinolin-6-yl]-urea;
1-[2-((R)-Indan-1-ylamino)-quinolin-6-yl]-3-(2-morpholin-4-yl-pyridin-4-yl)-urea;
N'-{2-[(1R)-2,3-dihydro-1H-inden-1-ylamino]quinolin-6-yl}-N-(4-methoxyphenyl)-N-methylsulfamide;
N'-{2-[(1R)-2,3-dihydro-1H-inden-1-ylamino]quinolin-6-yl}-N-methyl-N-(4-methylphenyl)sulfamide;
1-{2-[(1R)-2,3-dihydro-1H-inden-1-ylamino]quinolin-6-yl}-3-[4-(pentafluoro-sulfanyl)phenyl]urea;
N-(4-chlorophenyl)-N'-{2-[(1R)-2,3-dihydro-1H-inden-1-ylamino]quinolin-6-yl}-N-methylsulfamide;
N'-{2-[(1R)-2,3-dihydro-1H-inden-1-ylamino]quinolin-6-yl}-N-(4-fluorophenyl)-N-methylsulfamide;
1-(3,5-Dimethyl-isoxazol-4-yl)-3-[2-((R)-indan-1-ylamino)-quinolin-6-yl]-urea;
N'-{2-[(1R)-2,3-dihydro-1H-inden-1-ylamino]quinolin-6-yl}-N-methyl-N-(4-methylbenzyl)sulfamide; and
1-[2-((R)-Indan-1-ylamino)-quinolin-6-yl]-3-pyridin-2-yl-urea.

23. The compound of claim 1, selected from the group consisting of
1-[2-((R)-Indan-1-ylamino)-quinolin-6-yl]-3-(3-methyl-3H-imidazol-4-ylmethyl)-urea;
N-(4-chlorobenzyl)-N'-{2-[(1R)-2,3-dihydro-1H-inden-1-ylamino]quinolin-6-yl}-N-methylsulfamide;
[2-((R)-Indan-1-ylamino)-quinolin-6-yl]-carbamic acid 4-methoxy-phenyl ester;
N-(3-chlorophenyl)-N'-{2-[(1R)-2,3-dihydro-1H-inden-1-ylamino]quinolin-6-yl}-N-methylsulfamide;
N-[2-((R)-Indan-1-ylamino)-quinolin-6-yl]-2-thiophen-2-yl-acetamide;
4-Fluoro-N-[2-((R)-indan-1-ylamino)-quinolin-6-yl]-benzamide;
2-(4-Fluoro-phenyl)-N-[2-((R)-indan-1-ylamino)-quinolin-6-yl]-acetamide;
2-((R)-Indan-1-ylamino)-quinoline-6-carboxylic acid 4-fluoro-benzylamide;
(R)-Indan-1-yl-[6-(5-methyl-[1,2,4]oxadiazol-3-yl)-quinolin-2-yl]-amine;
4-Fluoro-N-[2-((R)-indan-1-ylamino)-quinolin-6-ylmethyl]-benzamide; and
2-((R)-Indan-1-ylamino)-quinoline-6-carboxylic acid 2-methoxy-benzylamide.

24. The compound of claim 1, selected from the group consisting of
(4-Fluoro-phenyl)-[2-((R)-indan-1-ylamino)-quinolin-6-yl]-methanone oxime;
2-((R)-Indan-1-ylamino)-quinoline-6-carboxylic acid (2,6-dimethoxy-phenyl)-amide;
1-[2-((R)-Indan-1-ylamino)-quinolin-6-yl]-3-(2-methyl-2H-pyrazol-3-yl)-urea;
1-[2-((R)-Indan-1-ylamino)-quinolin-6-yl]-3-(2H-[1,2,4]triazol-3-yl)-urea;
1-[2-((R)-Indan-1-ylamino)-quinolin-6-yl]-3-thiazol-2-yl-urea;
(6-Imidazol-1-yl-quinolin-2-yl)-(R)-indan-1-yl-amine;
(R)-Indan-1-yl-(6-[1,2,4]triazol-1-yl-quinolin-2-yl)-amine;
1-Benzoyl-3-[2-((R)-indan-1-ylamino)-quinolin-6-yl]-thiourea;

{6-[(4-Fluoro-benzylamino)-methyl]-quinolin-2-yl}-(R)-indan-1-yl-amine;
N-Benzyl-N'-[2-((R)-indan-1-ylamino)-quinolin-6-yl]-guanidine; and
N²—(R)-Indan-1-yl-N6-pyrimidin-2-yl-quinoline-2,6-diamine.

25. The compound of claim 1, selected from the group consisting of
N⁶-(4,6-Dimethyl-pyrimidin-2-yl)-N²—(R)-indan-1-yl-quinoline-2,6-diamine;
N²—(R)-Indan-1-yl-N⁶-(4-methyl-pyrimidin-2-yl)-quinoline-2,6-diamine;
N²—(R)-Indan-1-yl-N⁶-pyridin-2-yl-quinoline-2,6-diamine;
N²—(R)-Indan-1-yl-N⁶-(3-methyl-pyridin-2-yl)-quinoline-2,6-diamine;
N⁶-(2-Ethyl-2H-tetrazol-5-yl)-N²—(R)-indan-1-yl-quinoline-2,6-diamine;
N²—(R)-Indan-1-yl-N⁶-(6-methyl-pyridin-2-yl)-quinoline-2,6-diamine;
N²—(R)-Indan-1-yl-N⁶-(4-trifluoromethyl-pyrimidin-2-yl)-quinoline-2,6-diamine;
N²—(R)-Indan-1-yl-N⁶-(5-methyl-isoxazol-3-yl)-quinoline-2,6-diamine;
N⁶-(2-tert-Butyl-2H-tetrazol-5-yl)-N²—(R)-indan-1-yl-quinoline-2,6-diamine; and
N⁶-(5-Cyclopropyl-[1,3,4]oxadiazol-2-yl)-N²—(R)-indan-1-yl-quinoline-2,6-diamine.

26. The compound of claim 1, selected from the group consisting of
N²—(R)-Indan-1-yl-N⁶-(5-methyl-[1,3,4]oxadiazol-2-yl)-quinoline-2,6-diamine;
N²—(R)-Indan-1-yl-N⁶-(3-methyl-[1,2,4]oxadiazol-5-yl)-quinoline-2,6-diamine;
N²—(R)-Indan-1-yl-N⁶-(5-trifluoromethyl-[1,3,4]oxadiazol-2-yl)-quinoline-2,6-diamine;
N²—(R)-Indan-1-yl-N⁶-(6-trifluoromethyl-pyridin-2-yl)-quinoline-2,6-diamine;
N²—(R)-Indan-1-yl-N⁶-oxazol-2-yl-quinoline-2,6-diamine;
N²—(R)-Indan-1-yl-N⁶-(5-methyl-benzoxazol-2-yl)-quinoline-2,6-diamine;
2-{3-[2-((R)-Indan-1-ylamino)-quinolin-6-ylamino]-phenyl}-ethanol;
N²—(R)-Indan-1-yl-N⁶-(3-piperidin-1-yl-[1,2,4]oxadiazol-5-yl)-quinoline-2,6-diamine;
N²—(R)-Indan-1-yl-N⁶-methyl-N⁶-pyridin-2-yl-quinoline-2,6-diamine; and
N²—(R)-Indan-1-yl-N⁶-(5-methoxymethyl-[1,3,4]oxadiazol-2-yl)-quinoline-2,6-diamine.

27. The compound of claim 1, selected from the group consisting of
N²—(R)-Indan-1-yl-N⁶-(3-morpholin-4-yl-[1,2,4]oxadiazol-5-yl)-quinoline-2,6-diamine;
N²—(R)-Indan-1-yl-N⁶-(3-phenyl-[1,2,4]oxadiazol-5-yl)-quinoline-2,6-diamine;
N²—(R)-Indan-1-yl-N⁶-[3-(4-methyl-piperazin-1-yl)-[1,2,4]oxadiazol-5-yl]-quinoline-2,6-diamine;
rac-N-[2-(5-Fluoro-indan-1-ylamino)-quinolin-6-yl]-2-pyridin-4-yl-acetamide;
rac-N²-(7-Methoxy-indan-1-yl)-N⁶-(6-trifluoromethyl-pyridin-2-yl)-quinoline-2,6-diamine;
rac-N²-(7-Methoxy-indan-1-yl)-N⁶-(4-trifluoromethyl-pyrimidin-2-yl)-quinoline-2,6-diamine;
rac-N⁶-(4,6-Dimethyl-pyrimidin-2-yl)-N²-(7-methoxy-indan-1-yl)-quinoline-2,6-diamine;
rac-N²-(7-Methoxy-indan-1-yl)-N⁶-(6-methyl-pyridin-2-yl)-quinoline-2,6-diamine;
rac-N²-(7-Methoxy-indan-1-yl)-N⁶-(5-methyl-isoxazol-3-yl)-quinoline-2,6-diamine; and
rac-N²-(2,3-Dihydro-benzofuran-3-yl)-N⁶-(6-trifluoromethyl-pyridin-2-yl)-quinoline-2,6-diamine.

28. The compound of claim 1, selected from the group consisting of
rac-N²-(2,3-Dihydro-benzofuran-3-yl)-N⁶-(4,6-dimethyl-pyrimidin-2-yl)-quinoline-2,6-diamine;
rac-N²-(2,3-Dihydro-benzofuran-3-yl)-N⁶-(4-trifluoromethyl-pyrimidin-2-yl)-quinoline-2,6-diamine;
rac-N²-(2,3-Dihydro-benzofuran-3-yl)-N⁶-(6-methyl-pyridin-2-yl)-quinoline-2,6-diamine;
rac-2-Imidazol-1-yl-N-[2-(7-methoxy-indan-1-ylamino)-quinolin-6-yl]-acetamide;
rac-N²-(2,3-Dihydro-benzofuran-3-yl)-N⁶-(5-methyl-isoxazol-3-yl)-quinoline-2,6-diamine;
rac-N²-(5-Fluoro-indan-1-yl)-N⁶-(6-trifluoromethyl-pyridin-2-yl)-quinoline-2,6-diamine;
rac-N²-(5-Fluoro-indan-1-yl)-N⁶-(4-trifluoromethyl-pyrimidin-2-yl)-quinoline-2,6-diamine;
rac-N⁶-(4,6-Dimethyl-pyrimidin-2-yl)-N²-(7-methoxy-indan-1-yl)-quinoline-2,6-diamine;
rac-N²-(5-Fluoro-indan-1-yl)-N⁶-(6-methyl-pyridin-2-yl)-quinoline-2,6-diamine; and
rac-N²-(5-Fluoro-indan-1-yl)-N⁶-(5-methyl-isoxazol-3-yl)-quinoline-2,6-diamine.

29. The compound of claim 1, selected from the group consisting of
rac-N-[2-(7-Fluoro-indan-1-ylamino)-quinolin-6-yl]-2-[1,2,4]triazol-1-yl-acetamide;
rac-N-[2-(7-Fluoro-indan-1-ylamino)-quinolin-6-yl]-2-thiazol-4-yl-acetamide;
rac-N²-(4-Methoxy-2,3-dihydro-benzofuran-3-yl)-N⁶-(6-trifluoromethyl-pyridin-2-yl)-quinoline-2,6-diamine;
rac-N²-(4-Methoxy-2,3-dihydro-benzofuran-3-yl)-N⁶-(4-trifluoromethyl-pyrimidin-2-yl)-quinoline-2,6-diamine;
rac-N⁶-(4,6-Dimethyl-pyrimidin-2-yl)-N²-(4-methoxy-2,3-dihydro-benzofuran-3-yl)-quinoline-2,6-diamine;
rac-N²-(4-Methoxy-2,3-dihydro-benzofuran-3-yl)-N⁶-(6-methyl-pyridin-2-yl)-quinoline-2,6-diamine;
rac-N²-(4-Methoxy-2,3-dihydro-benzofuran-3-yl)-N⁶-(5-methyl-isoxazol-3-yl)-quinoline-2,6-diamine;
rac-N-[2-(7-Methoxy-indan-1-ylamino)-quinolin-6-yl]-2-[1,2,4]triazol-4-yl-acetamide
rac-N-[2-(7-Methoxy-indan-1-ylamino)-quinolin-6-yl]-2-pyridin-4-yl-acetamide.

30. A pharmaceutical composition comprising a therapeutically effective amount of a compound of formula I

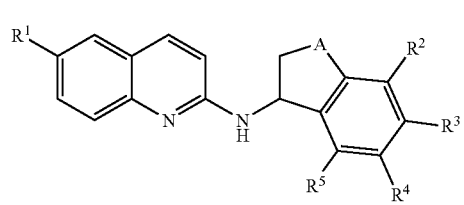

wherein
A is —CH₂— or —O—,
R¹ is 5-membered heteroaryl, —C(=NRᵃ)—Ar¹, —NRᵇ—Ar¹, —C(O)—NH—Ar¹, —NH—C(O)—Ar¹, —NH—S(O)₂—Ar¹, —NH—CH₂—Ar¹, —O—CH$_2$—Ar$^1$, —CH$_2$—NH—C(O)—Ar$^1$, —C(O)—NH—CH$_2$—Ar$^1$, —CH$_2$—NH—CH$_2$—Ar$^1$, —NH—S(O)$_2$—NR$^c$—Ar$^1$, —NR$^d$—C(O)—NR$^e$—Ar$^1$, —NH—C(O)—CH$_2$—Ar$^1$, —NH—C(O)—O—Ar$^1$, —NH—C(O)—NH—CHR$^f$—Ar$^1$, —NH—C(=NR$^a$)—NH—CH$_2$—Ar$^1$, —NH—(CH$_2$)$_3$—Ar$^1$, or —NH—C(S)—NH—C(O)—Ar$^1$, R$^a$ is H, OH, or alkyl, R$^b$, R$^c$, R$^d$, R$^e$, and R$^f$ are each independently H, alkyl, or allyl, Ar$^1$ is phenyl or 5- to 10-membered monocyclic or bicyclic heteroaryl, each of which is unsubstituted or substituted by one or more halo, CN, NO$_2$, NH$_2$, OH, alkyl, haloalkyl, hydroxyalkyl, cyanoalkyl, cycloalkyl, -alkylene-cycloalkyl, -alkylene-O-alkyl, alkoxy, haloalkoxy, —S(O)$_2$-alkyl, —S(O)$_2$-cycloalkyl, —SF$_5$, or 5- to 6-membered heterocycloalkyl, wherein cycloalkyl or heterocycloalkyl are each unsubstituted or substituted independently by one or more oxo, halo, alkyl, hydroxy, hydroxyalkyl, haloalkyl or alkyoxy, R$^2$, R$^3$, R$^4$ and R$^5$ are independently selected from H, halo, alkyl and alkoxy;

or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 8,188,284 B2
APPLICATION NO. : 12/394072
DATED : May 29, 2012
INVENTOR(S) : Kolczewski et al.

Page 1 of 1

It is certified that error appears in the above-identified patent and that said Letters Patent is hereby corrected as shown below:

TITLE PAGE Item 73:

• The Assignee information reads: "Hoffman-La Roche Inc., Nutley, NJ (US)". The Assignee information should read --- Hoffmann-La Roche Inc., Nutley, NJ (US) ---.

Signed and Sealed this
Eleventh Day of September, 2012

David J. Kappos
*Director of the United States Patent and Trademark Office*